(12) United States Patent
Tennican et al.

(10) Patent No.: US 7,749,189 B2
(45) Date of Patent: Jul. 6, 2010

(54) SYRINGE DEVICES AND METHODS FOR MIXING AND ADMINISTERING MEDICATION

(75) Inventors: Patrick O. Tennican, Spokane, WA (US); Russell A. Michaelsen, Spokane, WA (US); L. Myles Phipps, Shelton, WA (US)

(73) Assignee: Hyprotek, Inc., Spokane, WA (US)

( * ) Notice: Subject to any disclaimer, the term of this patent is extended or adjusted under 35 U.S.C. 154(b) by 165 days.

(21) Appl. No.: 11/751,438

(22) Filed: May 21, 2007

(65) Prior Publication Data

US 2007/0276322 A1    Nov. 29, 2007

Related U.S. Application Data

(62) Division of application No. 11/238,880, filed on Sep. 28, 2005.

(60) Provisional application No. 60/670,413, filed on Apr. 11, 2005, provisional application No. 60/618,639, filed on Oct. 13, 2004.

(51) Int. Cl.
*A61M 37/00* (2006.01)
(52) U.S. Cl. ...................................... 604/88
(58) Field of Classification Search ............ 604/88
See application file for complete search history.

(56) References Cited

U.S. PATENT DOCUMENTS

| | | |
|---|---|---|
| 730,054 A | 6/1903 | Sheets |
| 984,037 A | 2/1911 | Sheets |
| 1,100,799 A | 6/1914 | Wedig |
| 1,465,793 A | 8/1923 | Schilling |
| 1,696,018 A | 12/1928 | Schellberg |
| 1,707,880 A | 4/1929 | Sheets |
| 2,453,590 A | 11/1948 | Poux |
| 2,540,461 A | 2/1951 | Smith |

(Continued)

FOREIGN PATENT DOCUMENTS

CA    2513165 A1    8/2004

(Continued)

OTHER PUBLICATIONS http://www.duoject.com/flash/duoject.html (2 pages).

(Continued)

*Primary Examiner*—Nicholas D Lucchesi
*Assistant Examiner*—Jason Flick
(74) *Attorney, Agent, or Firm*—Wells St. John P.S.

(57) ABSTRACT

The invention includes a device having a chamber within a syringe. A fluid passageway extends through a syringe piston. A valve is associated with the passageway controlling fluid passage through the piston. The invention includes a piercing structure having a head segment and a body portion, with a channel through the body portion and through at least one surface of the head without passing through the tip. In another aspect the invention encompasses a method of preparing an agent for administration to an individual. A first component is provided within a syringe and a second component is provided within a vial. A closed valve is associated with a fluid passageway between the vial and the syringe barrel through a piston. Valve repositioning allows fluid passage and sliding of the piston joins the first and second components. Repeated sliding of the piston mixes the components to produce the medication agent.

8 Claims, 17 Drawing Sheets

U.S. PATENT DOCUMENTS

| | | | |
|---|---|---|---|
| 2,555,878 A | 6/1951 | Drabicki |
| 2,661,740 A | 12/1953 | Hickey |
| 2,677,372 A | 5/1954 | Barnish |
| 2,693,186 A | 11/1954 | Riker et al. |
| 2,818,999 A | 1/1958 | Miller |
| 2,842,124 A | 7/1958 | James |
| 2,869,544 A | 1/1959 | Ratcliff et al. |
| 3,052,239 A | 9/1962 | Silver et al. |
| 3,052,240 A | 9/1962 | Silver et al. |
| 3,164,303 A | 1/1965 | Trautmann |
| 3,342,180 A | 9/1967 | Sandhage et al. |
| 3,348,546 A | 10/1967 | Roberts et al. |
| 3,511,239 A | 5/1970 | Tuschhoff |
| 3,645,268 A | 2/1972 | Capote |
| 3,648,704 A | 3/1972 | Jackson |
| 3,659,602 A | 5/1972 | Cloyd |
| 3,844,318 A | 10/1974 | Raia et al. |
| 3,938,520 A | 2/1976 | Scislowicz et al. |
| 3,946,732 A | 3/1976 | Hurscham |
| 4,014,330 A | 3/1977 | Genese |
| 4,031,892 A | 6/1977 | Hurschman |
| 4,044,757 A | 8/1977 | McWhorter et al. |
| 4,116,240 A | 9/1978 | Guiney |
| 4,142,633 A | 3/1979 | Raghavachari et al. |
| 4,153,057 A | 5/1979 | Kobel |
| 4,164,203 A | 8/1979 | Cavanagh |
| 4,166,533 A * | 9/1979 | Maitland | 206/366 |
| 4,191,225 A | 3/1980 | Ogle |
| 4,244,364 A | 1/1981 | Grushkin |
| 4,303,069 A | 12/1981 | Cohen |
| 4,328,802 A | 5/1982 | Curley et al. |
| 4,405,317 A | 9/1983 | Case |
| 4,424,057 A | 1/1984 | House |
| 4,464,174 A | 8/1984 | Ennis |
| 4,518,386 A | 5/1985 | Tartaglia |
| 4,585,446 A | 4/1986 | Kempf |
| 4,589,879 A | 5/1986 | Pearson |
| 4,591,357 A | 5/1986 | Sneider |
| 4,599,082 A | 7/1986 | Grimard |
| 4,624,667 A | 11/1986 | Rutnarak |
| 4,657,534 A | 4/1987 | Beck et al. |
| 4,685,596 A | 8/1987 | Mattheis |
| 4,700,872 A | 10/1987 | Keyes et al. |
| 4,722,733 A | 2/1988 | Howson |
| 4,735,608 A | 4/1988 | Sardam |
| 4,758,231 A | 7/1988 | Haber et al. |
| 4,759,750 A | 7/1988 | DeVries et al. |
| 4,781,701 A | 11/1988 | Geprags |
| 4,838,855 A | 6/1989 | Lynn |
| 4,861,335 A | 8/1989 | Reynolds |
| 4,874,381 A | 10/1989 | Vetter |
| 4,886,495 A | 12/1989 | Reynolds |
| 4,898,209 A | 2/1990 | Zbed |
| 4,969,883 A | 11/1990 | Gilbert et al. |
| 4,994,029 A | 2/1991 | Rohrbough |
| 4,997,420 A | 3/1991 | LeFevre |
| 5,067,948 A | 11/1991 | Haber et al. |
| 5,069,670 A | 12/1991 | Vetter et al. |
| 5,080,649 A | 1/1992 | Vetter |
| 5,098,402 A | 3/1992 | Davis |
| 5,135,496 A | 8/1992 | Vetter et al. |
| 5,137,511 A | 8/1992 | Reynolds |
| 5,139,490 A | 8/1992 | Vetter et al. |
| 5,147,329 A | 9/1992 | Brannon |
| 5,171,214 A | 12/1992 | Kolber et al. |
| 5,181,909 A | 1/1993 | McFarlane |
| 5,226,900 A | 7/1993 | Bancsi et al. |
| 5,247,972 A | 9/1993 | Tetreault |
| 5,290,228 A | 3/1994 | Uemura et al. |
| 5,312,336 A | 5/1994 | Haber et al. |
| 5,320,603 A | 6/1994 | Vetter et al. |
| 5,330,426 A | 7/1994 | Kriesel et al. |
| 5,334,163 A * | 8/1994 | Sinnett | 604/236 |
| 5,356,375 A | 10/1994 | Higley |
| 5,356,380 A | 10/1994 | Hoekwater et al. |
| 5,364,369 A | 11/1994 | Reynolds |
| 5,372,590 A | 12/1994 | Haber et al. |
| 5,393,497 A | 2/1995 | Haber et al. |
| 5,407,070 A | 4/1995 | Bascos et al. |
| 5,411,489 A | 5/1995 | Pagay et al. |
| 5,411,499 A | 5/1995 | Dudar et al. |
| 5,423,751 A | 6/1995 | Harrison et al. |
| 5,437,648 A | 8/1995 | Graves et al. |
| 5,466,219 A | 11/1995 | Lynn et al. |
| 5,466,220 A * | 11/1995 | Brenneman | 604/87 |
| 5,470,327 A | 11/1995 | Helgren et al. |
| 5,472,403 A | 12/1995 | Cornacchia et al. |
| 5,478,314 A | 12/1995 | Malenchek |
| 5,478,337 A | 12/1995 | Okamoto et al. |
| 5,484,406 A | 1/1996 | Wong et al. |
| 5,489,266 A | 2/1996 | Grimard |
| 5,505,704 A | 4/1996 | Pawelka et al. |
| 5,531,672 A | 7/1996 | Lynn |
| 5,531,683 A | 7/1996 | Kriesel et al. |
| 5,533,994 A | 7/1996 | Meyer |
| 5,549,569 A | 8/1996 | Lynn et al. |
| 5,566,729 A | 10/1996 | Grabenkort et al. |
| 5,569,191 A | 10/1996 | Meyer |
| 5,569,193 A | 10/1996 | Hofstetter et al. |
| 5,580,351 A | 12/1996 | Helgren et al. |
| 5,584,819 A | 12/1996 | Kopfer |
| 5,618,268 A | 4/1997 | Raines et al. |
| 5,630,800 A | 5/1997 | Blank et al. |
| 5,637,100 A | 6/1997 | Sudo |
| 5,647,845 A | 7/1997 | Haber et al. |
| 5,653,686 A | 8/1997 | Coulter et al. |
| 5,674,195 A | 10/1997 | Truthan |
| 5,685,866 A | 11/1997 | Lopez |
| 5,722,950 A | 3/1998 | Fujita et al. |
| 5,738,655 A | 4/1998 | Vallelunga et al. |
| 5,766,147 A | 6/1998 | Sancoff et al. |
| 5,769,825 A | 6/1998 | Lynn |
| 5,772,665 A | 6/1998 | Glad et al. |
| 5,776,125 A | 7/1998 | Dudar et al. |
| 5,785,701 A | 7/1998 | Sams et al. |
| 5,795,337 A | 8/1998 | Grimard |
| 5,807,323 A | 9/1998 | Kriesel et al. |
| 5,827,262 A | 10/1998 | Neftel et al. |
| 5,833,653 A | 11/1998 | Vetter et al. |
| 5,842,326 A | 12/1998 | Wolf |
| 5,897,527 A | 4/1999 | Tsukada |
| 5,928,215 A | 7/1999 | Caizza et al. |
| RE36,273 E | 8/1999 | Brannon |
| 5,976,115 A | 11/1999 | Parris et al. |
| 5,989,227 A | 11/1999 | Vetter et al. |
| 6,027,472 A | 2/2000 | Kriesel et al. |
| 6,065,270 A | 5/2000 | Reinhard et al. |
| 6,099,511 A | 8/2000 | Devos et al. |
| 6,149,623 A | 11/2000 | Reynolds |
| 6,267,154 B1 | 7/2001 | Felicelli et al. |
| 6,280,430 B1 | 8/2001 | Neftel et al. |
| 6,319,225 B1 | 11/2001 | Sugita et al. |
| 6,349,850 B1 | 2/2002 | Cheikh |
| 6,358,236 B1 | 3/2002 | DeFoggi et al. |
| 6,364,866 B1 | 4/2002 | Furr et al. |
| 6,379,328 B1 | 4/2002 | Mac Clay |
| 6,391,014 B1 | 5/2002 | Silverman |
| 6,478,788 B1 | 11/2002 | Aneas |
| 6,478,808 B2 | 11/2002 | Nowakowski |
| 6,488,651 B1 | 12/2002 | Morris et al. |
| 6,491,665 B1 | 12/2002 | Vetter et al. |
| 6,527,738 B1 | 3/2003 | Jones et al. |
| 6,544,233 B1 | 4/2003 | Fukui et al. |
| 6,576,224 B1 | 6/2003 | Osbakken et al. |

| | | |
|---|---|---|
| 6,591,876 B2 | 7/2003 | Safabash |
| 6,599,264 B1 | 7/2003 | Erni et al. |
| 6,599,273 B1 | 7/2003 | Lopez |
| 6,602,223 B2 | 8/2003 | Szapiro et al. |
| 6,626,309 B1 | 9/2003 | Jansen et al. |
| 6,638,244 B1 | 10/2003 | Reynolds |
| 6,650,929 B1 | 11/2003 | Nemoto et al. |
| 6,681,946 B1 | 1/2004 | Jansen et al. |
| 6,716,193 B1 | 4/2004 | Neftel |
| 6,729,370 B2 * | 5/2004 | Norton et al. ............... 141/329 |
| 6,743,214 B2 | 6/2004 | Heil et al. |
| 6,802,828 B2 | 10/2004 | Reynolds |
| 6,808,511 B2 | 10/2004 | Pond |
| 6,817,987 B2 | 11/2004 | Vetter et al. |
| 6,852,103 B2 | 2/2005 | Fowles et al. |
| 7,074,216 B2 | 7/2006 | Fowles et al. |
| 7,081,109 B2 | 7/2006 | Tighe et al. |
| 7,134,782 B2 | 11/2006 | Coffeen et al. |
| 7,452,344 B2 | 11/2008 | Jorgensen et al. |
| 2002/0002354 A1 | 1/2002 | Vetter et al. |
| 2002/0022804 A1 | 2/2002 | Connolly et al. |
| 2002/0061281 A1 | 5/2002 | Osbakken et al. |
| 2002/0065490 A1 | 5/2002 | Heinz et al. |
| 2002/0068896 A1 | 6/2002 | Robinson et al. |
| 2002/0087118 A1 * | 7/2002 | Reynolds et al. ............... 604/82 |
| 2002/0128628 A1 | 9/2002 | Fathallah |
| 2002/0177819 A1 | 11/2002 | Barker et al. |
| 2003/0069545 A1 | 4/2003 | Arm |
| 2003/0114798 A1 | 6/2003 | Langley et al. |
| 2003/0225378 A1 | 12/2003 | Wilkie et al. |
| 2004/0078993 A1 | 4/2004 | Vetter et al. |
| 2004/0112457 A1 | 6/2004 | Norton et al. |
| 2004/0122345 A1 | 6/2004 | Muller |
| 2004/0167495 A1 | 8/2004 | Neftel |
| 2004/0182475 A1 | 9/2004 | Vetter et al. |
| 2004/0232171 A1 | 11/2004 | Bobst |
| 2004/0254525 A1 | 12/2004 | Uber, III et al. |
| 2005/0027259 A1 | 2/2005 | Vetter et al. |
| 2005/0070848 A1 | 3/2005 | Kim et al. |
| 2005/0090797 A1 | 4/2005 | Almasian et al. |
| 2005/0151652 A1 | 7/2005 | Frasch |
| 2005/0245881 A1 | 11/2005 | Meyer et al. |
| 2006/0027523 A1 | 2/2006 | Van Lintel et al. |
| 2006/0079834 A1 | 4/2006 | Tennican et al. |
| 2006/0178642 A1 | 8/2006 | Gillespie et al. |
| 2006/0184137 A1 | 8/2006 | Reynolds |
| 2006/0275336 A1 | 12/2006 | Du Plessis |
| 2006/0278588 A1 | 12/2006 | Woodell-May |
| 2008/0015496 A1 | 1/2008 | Hamedi-Sangsari |

FOREIGN PATENT DOCUMENTS

| | | |
|---|---|---|
| WO | 96/29113 A | 9/1996 |
| WO | 9937233 A1 | 7/1999 |
| WO | 00/13723 A | 3/2000 |
| WO | 0141666 A1 | 6/2001 |
| WO | 2004/064706 A | 8/2004 |
| WO | 2006044236 A2 | 4/2006 |

OTHER PUBLICATIONS http://www.life-assist.com/setfinder/preslit.html, ICU Medical/Setfinder Needle Free Products, pp. 1-6.

Clip'n. Ject [online] [retrieved on Nov. 9, 2005] retrieved from: http://www.westpharma.com/products/clip_n_Ject.asp? 1=0.

Debioclip Manual [online] [retrieved on Nov. 9, 2005] retrieved from: http://www.debiotech.com/products/drugdd/debioclip.html.

* cited by examiner

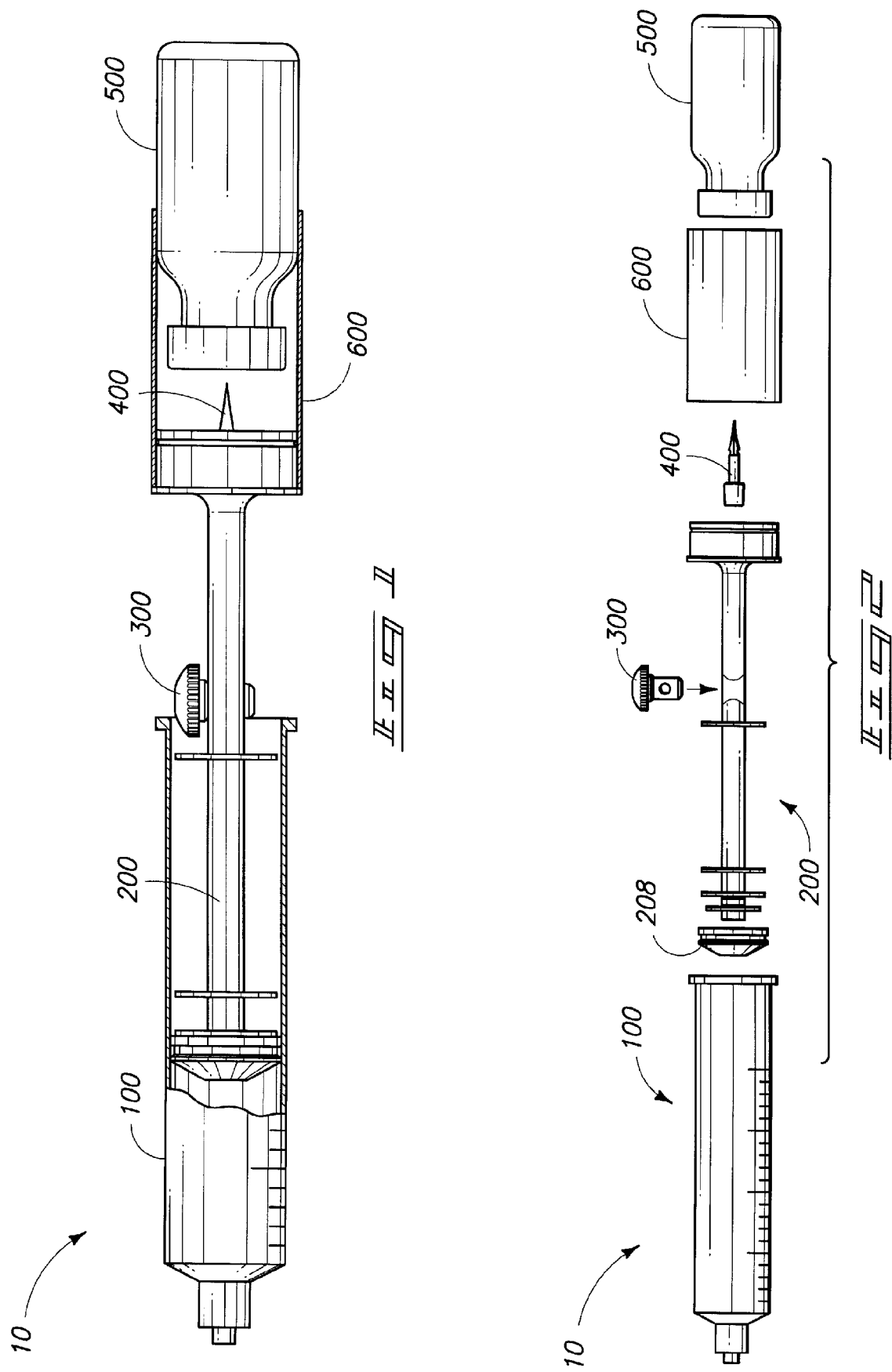

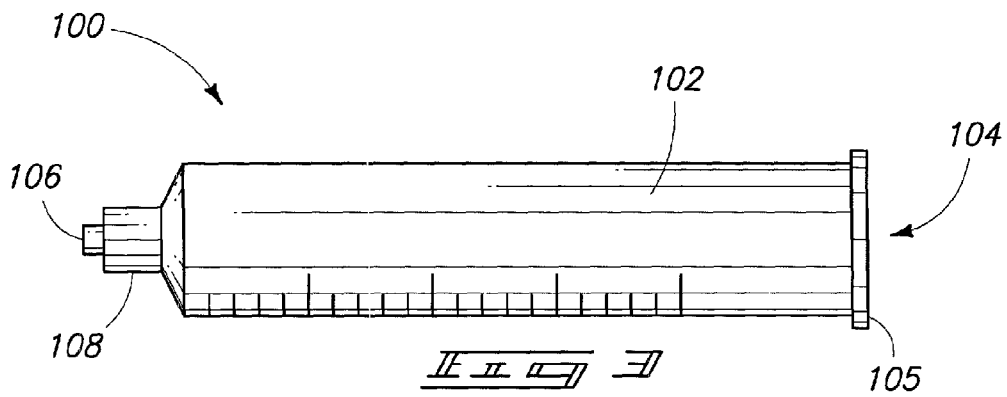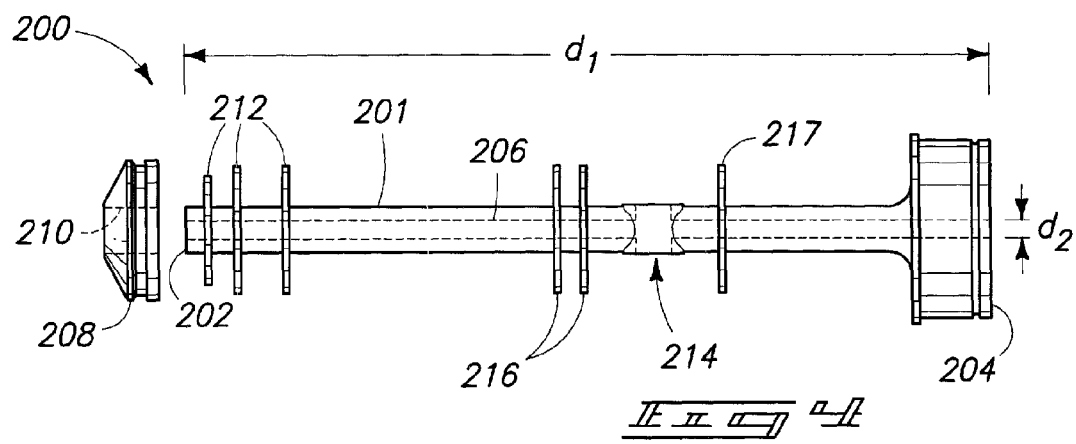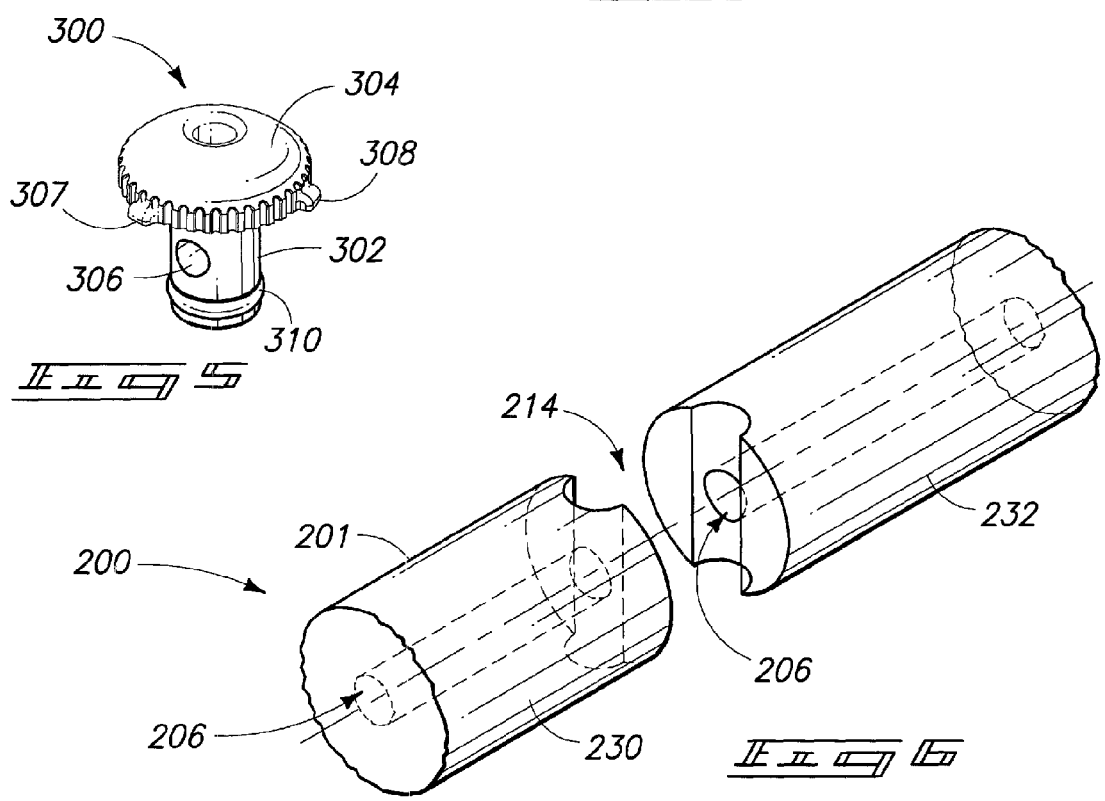

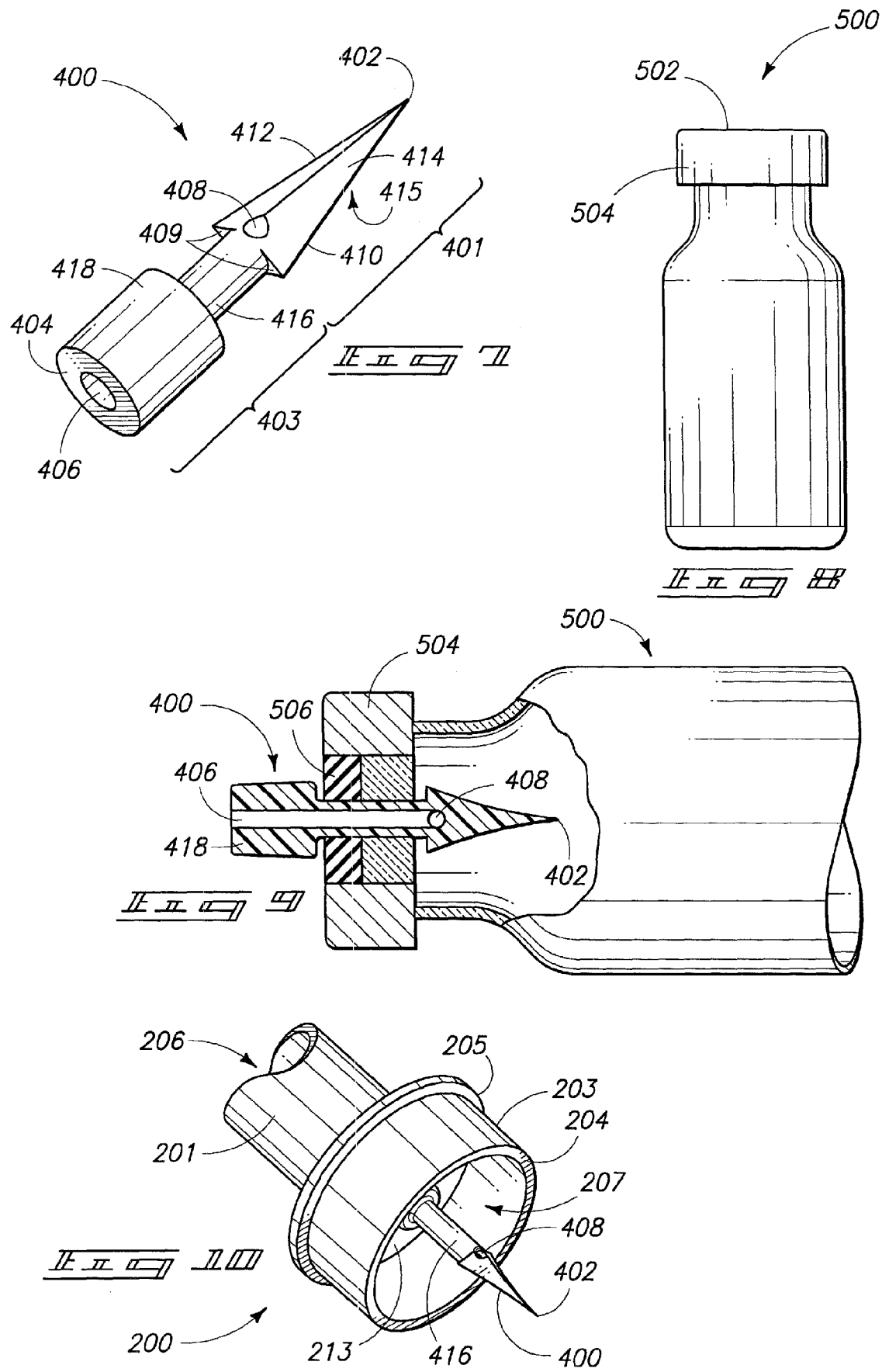

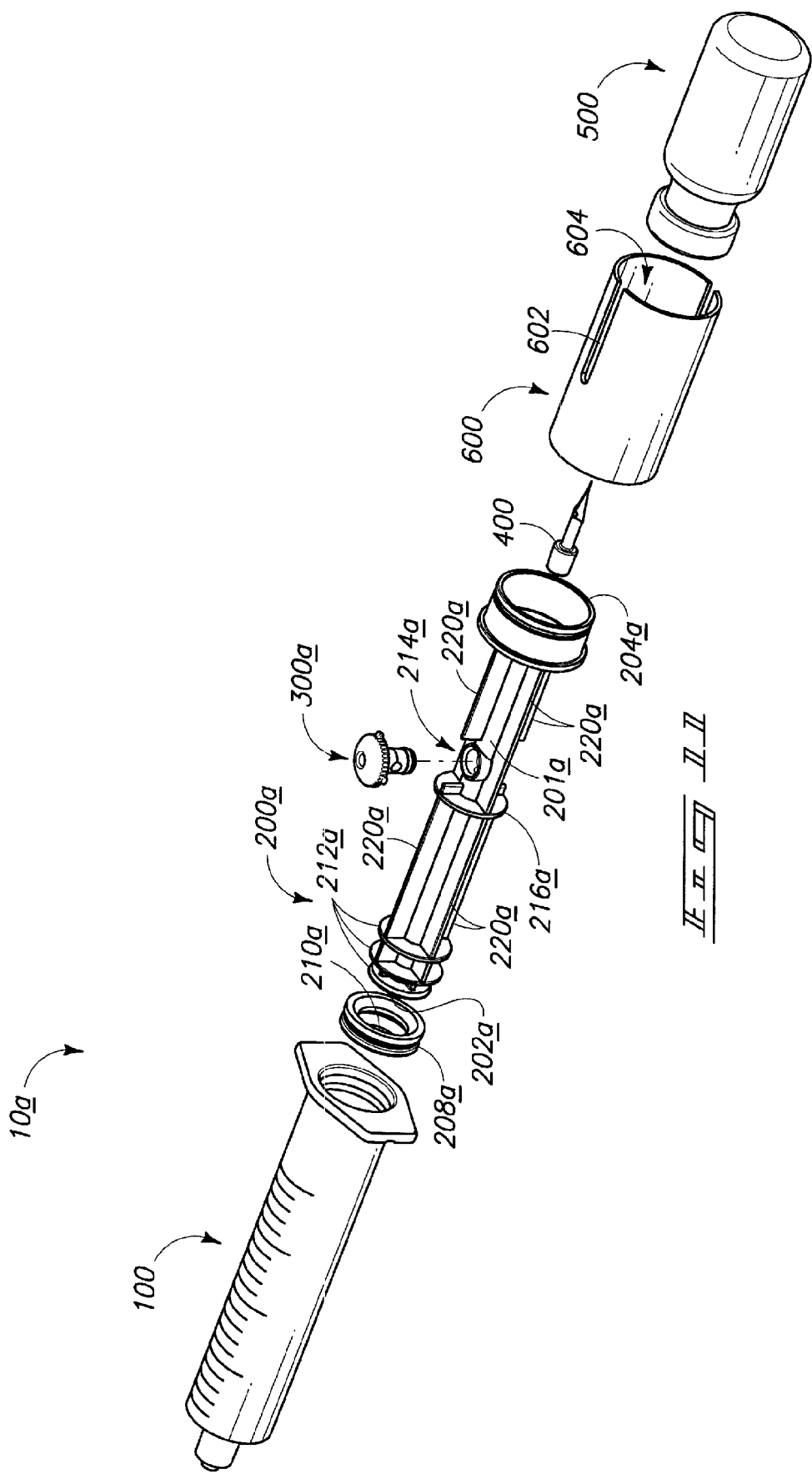

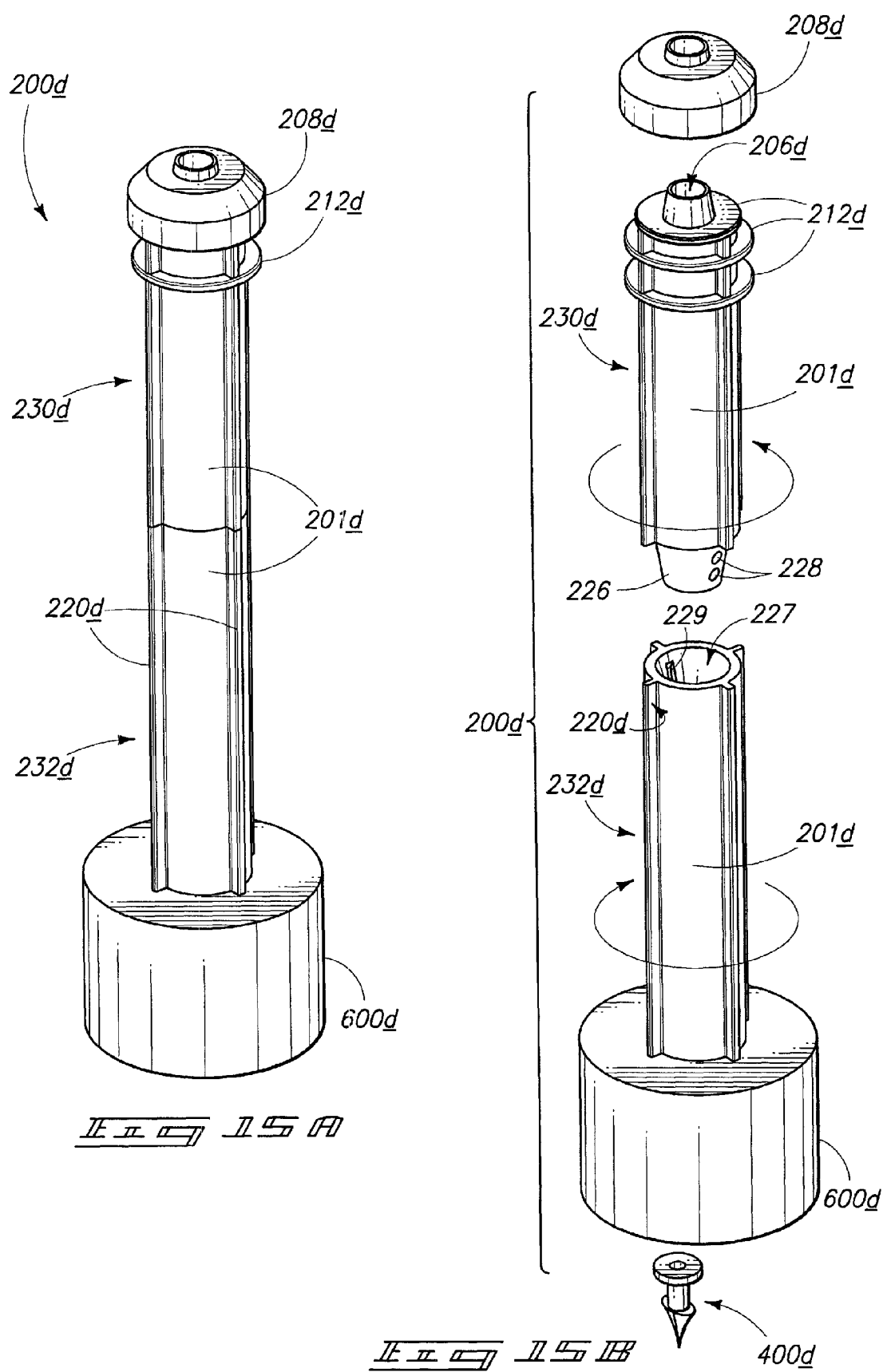

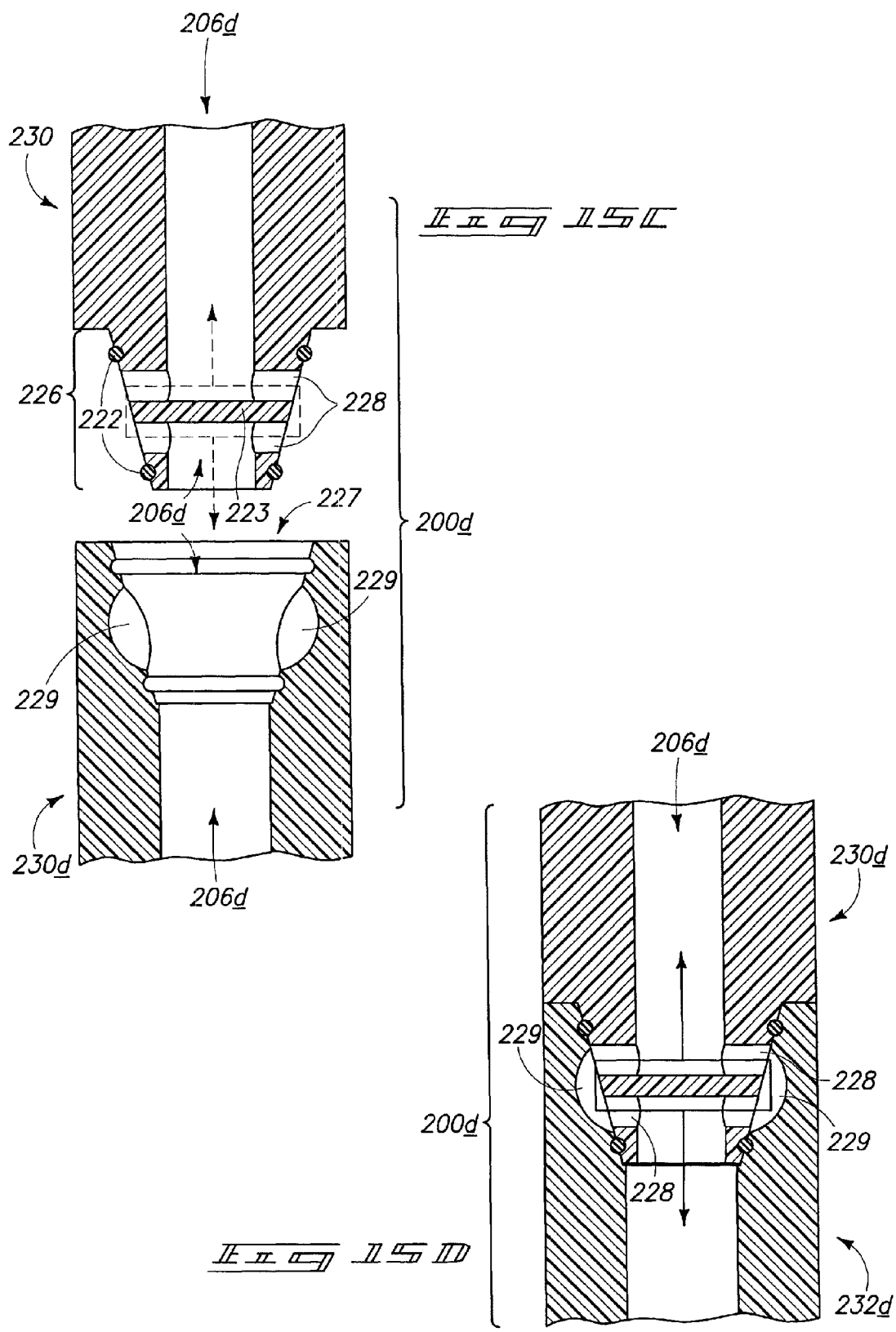

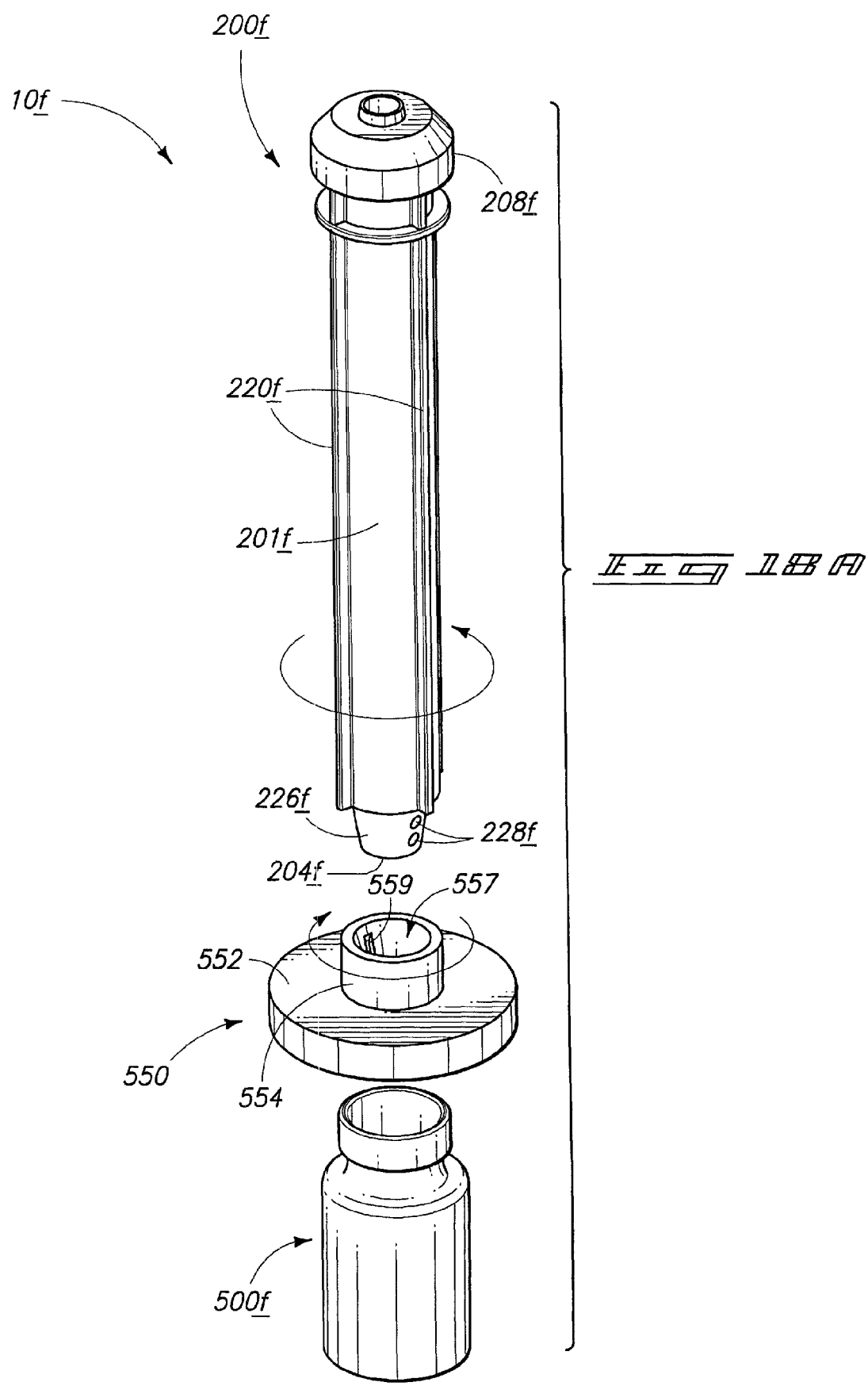

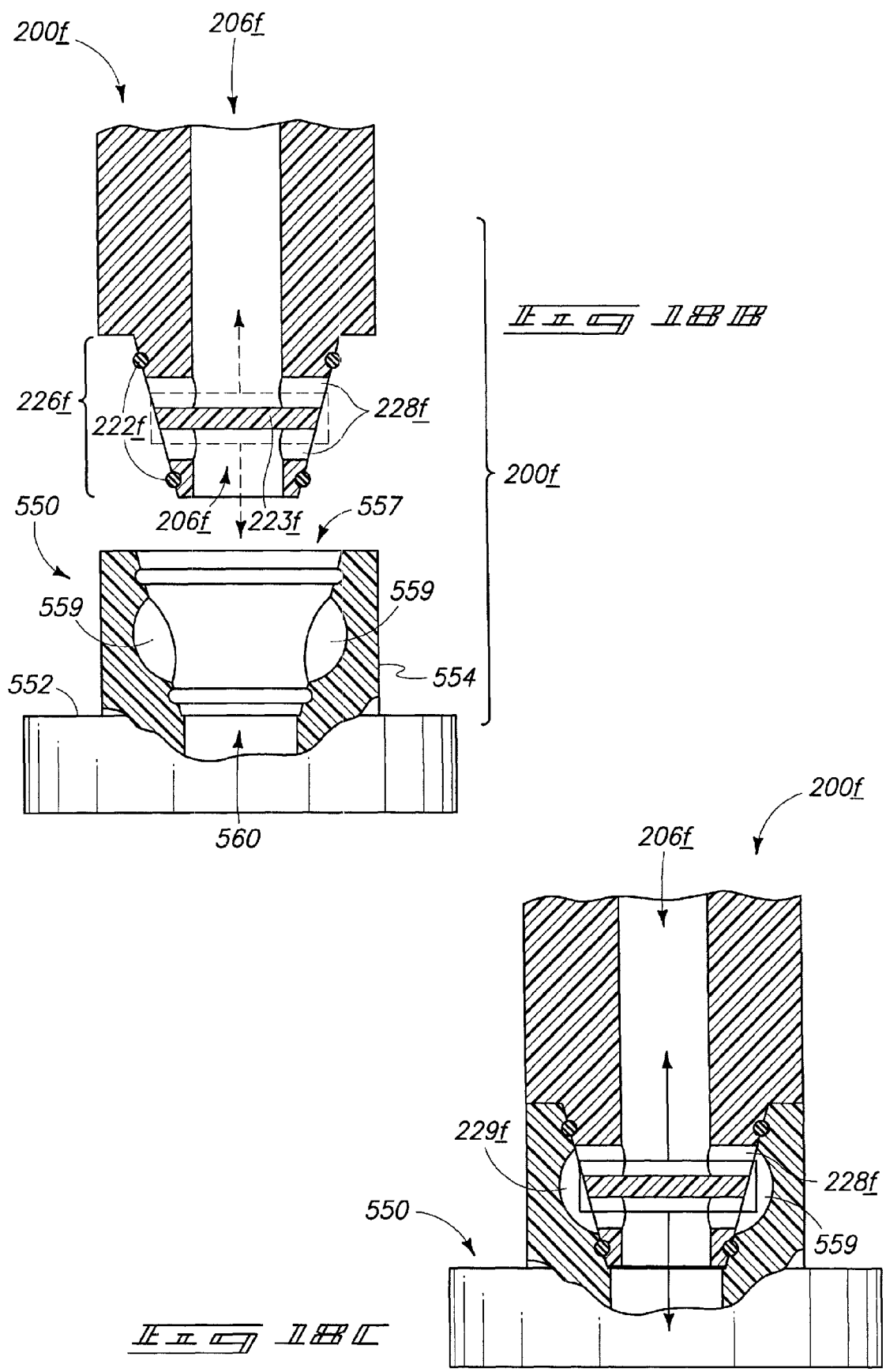

SYRINGE DEVICES AND METHODS FOR MIXING AND ADMINISTERING MEDICATION

RELATED PATENT DATA

This patent resulted from a divisional application of U.S. patent application Ser. No. 11/238,880, which was filed on Sep. 28, 2005 and claims priority under 35 U.S.C. §119 to U.S. Provisional Patent Application Ser. No. 60/670,413, which was filed Apr. 11, 2005, and to U.S. Provisional Patent Application Ser. No. 60/618,639, which was filed Oct. 13, 2004.

TECHNICAL FIELD

The method pertains to syringe devices, piercing structures, medication agent preparation systems, mixing and administration systems, methods of mixing components, and methods of preparing a medication agent for administration to an individual.

BACKGROUND OF THE INVENTION

Preparation of medicants or medication agents and administration of such agents to an individual often involves mixing of two or more components to form the agent and subsequent delivery of the mixed medicant to the individual. The mixing of components can typically involve extraction of one component in fluid form from a vial or other container and transfer of such components into a separate container which holds another component. In particular instances, only a portion of the contents of a vial or container is to be utilized for preparing a mixture prior to administering. Accordingly, the extraction and transfer can involve precise measuring of one or more components to be mixed.

A variety of problems may occur when utilizing conventional methodology and devices for mixing and/or administering medicants to an individual. For example, where multiple components are to be mixed, extraction and transfer of one component and introduction of such component into another component can potentially expose one or both of the components to a non-sterile or contaminated environment leading to contamination of the resulting medicant. Additionally, incomplete extraction or improper measurement of one or more components can result in preparation and/or administration of an improper dosage. In particular instances, once a medicant is mixed the mixture must again be extracted from a vial or container into a syringe prior to administering to an individual. Such additional transfer can lead to additional opportunities for contamination, incomplete extraction of contents and/or inaccurate measuring of a component or the resulting medicant. In practice, there is limited availability of sterile environments for maintaining sterility during transfer and/or mixing of components, or preparation and transfer of medicants. Additional errors can result from use of the wrong diluent to reconstitute the medication. Finally, preparation of medicants utilizing multiple components can be tedious and time consuming due to factors such as the need to access individually packaged items such as separate vials and/or transfer devices, or to measure one or more components to be combined to form the medicant.

It would be desirable to develop alternative methodology and systems for preparation and administration of medicants.

SUMMARY OF THE INVENTION

In one aspect the invention encompasses a syringe device. The device includes a syringe body having a cylindrical housing and a chamber within the housing. The device additionally includes a piston having a stem, a first end and a second end opposing the first end. The first end is external to the chamber comprised by the syringe body. A fluid passageway extends through the first end through the stem and through the second end of the piston. The syringe device further includes a valve which is associated with the fluid passageway through the piston such that the valve controls selective fluid passage through the piston. A cap can be reversibly attached to the syringe body to provide a fluid seal.

In one aspect the invention encompasses a piercing structure having a head segment comprising a tip disposed at a first end of the structure. The head has a front surface and an opposing back surface. The piercing structure additionally includes a body portion comprising a base surface disposed at a second end opposing the first end of the structure. A fluid passageway passes through the second end of the structure through the body portion and through at least one of the front surface and the back surface of the head without passing through the tip.

In one aspect the invention encompasses a medication agent preparation system. The system comprises a syringe having a barrel with an internal chamber, and a piston having a first end, a second end and a fluid passageway passing longitudinally through the piston. At least a portion of the piston comprising the first end is inserted into the chamber. A piercing structure having a fluid channel is associated with the second end of the piston. A vial is disposed proximate and moveable relative to the tip of the piercing structure. A first component of a medication agent is disposed within the internal chamber of the syringe barrel and second component of the medication agent is disposed within the vial. A valve is associated with the fluid passageway which passes through the piston.

In another aspect the invention encompasses a method of preparing a medication agent for administration to an individual. The method includes providing a syringe having a syringe barrel and a piston disposed at an initial position relative to the syringe barrel. A first component is provided within the syringe barrel and a second component is provided within a vial. A valve is associated with a fluid passageway between the vial and the syringe barrel with the valve initially being disposed in a closed position, blocking fluid passage through the passageway. The method includes repositioning the valve to allow fluid passage between the vial and the syringe barrel. After repositioning the valve, the piston is slid in a first direction to join the first component with the second component. The first and second components are mixed to produce the medication agent. Mixing can be facilitated by agitating, inverting the device and/or repeated sliding of the piston in opposing directions. The method further includes drawing the medication agent into the syringe barrel.

In an additional aspect the invention includes a method of preparing a composition. A packaging material is provided containing a mixing device in which the mixing device includes a housing having a chamber therein containing a first material. The device also includes a piston slideable within the chamber with the piston having a length that is greater than the length of the chamber. The mixing device further includes a container holding a second material. A fluid passageway is disposed longitudinally through the piston with a valve being associated with the fluid passageway. Without exposing the device to an environment external to the packaging material the valve is repositioned from a closed position to an open position. With the valve in the open position the piston is slid in a first direction from a first position within the chamber to a second position within the chamber. The sliding of the piston moves one of the first and second components through the piston. The first and second materials are then mixed to form a mixture where the mixing comprises sliding the piston in a second direction and subsequently returning the piston in the first direction. The mixture is then drawn into the chamber through the piston.

In one aspect the invention encompasses a medicant preparation device. The device includes a syringe barrel which has a first end, a second end and a longitudinal axis therebetween. A piston is insertable with the syringe barrel through the second end with the piston being slideable within the barrel. The device further includes a vial containing a material and an adapter component. The adapter component includes a vial housing portion configured to reversibly receive a vial. The adapter also has a fitting configured to attach to the syringe at the first end. A first fluid passageway extends through the fitting to a valve, and a second fluid passageway extends from the valve to the vial housing. The medicant preparation device additionally includes packaging which is configured to allow manipulation of the valve and sliding of the piston without opening of the package.

In a general aspect, the invention includes a device comprising a housing around a chamber, a piston having a first end, a second end and a fluid passageway between the first and second end with the piston being insertable into the chamber. The device also includes a valve associated with the fluid passageway such that flow through the fluid passageway is selectively regulated by the valve.

BRIEF DESCRIPTION OF THE DRAWINGS

Preferred embodiments of the invention are described below with reference to the following accompanying drawings.

FIG. 1 is a side view and partial cross-sectional view of a mixing assembly in accordance with one aspect of the invention.

FIG. 2 is an exploded side view of the assembly shown in FIG. 1.

FIG. 3 is a side view of a portion of a syringe device in accordance with one aspect of the invention.

FIG. 4 is a side view of a syringe piston in accordance with one aspect of the invention.

FIG. 5 is a perspective view of an exemplary valve according to one aspect of the invention.

FIG. 6 is a fragmented perspective view of a syringe piston in accordance with one aspect of the invention.

FIG. 7 is a perspective view of a piercing device in accordance with one aspect of the invention.

FIG. 8 is a side view of a container which can be utilized in one aspect of the invention.

FIG. 9 is a fragmentary side view and partial cross-sectional view of a portion of a mixing assembly as illustrated in FIG. 1.

FIG. 10 is a fragmentary perspective view of a portion of the mixing assembly illustrated in FIG. 1.

FIG. 11 is an exploded perspective view of a mixing assembly in accordance with an alternate aspect of the present invention.

FIG. 15A is a side view of an alternate embodiment of a piston in accordance with one aspect of the invention.

FIG. 15B is an exploded view of the piston structure shown in FIG. 15A.

FIG. 15C is an exploded cross-sectional fragmentary view of the piston structure shown in FIG. 15A.

FIG. 15D is a cross-sectional fragmentary sideview of the piston structure shown in FIG. 15A.

FIG. 18A is an exploded view of another alternate embodiment of a device in accordance with the invention.

FIG. 18B is an exploded fragmentary partially cross-sectional view of the device shown in FIG. 18A.

FIG. 18C is a fragmentary partially cross-sectional view of the device shown in FIG. 18A.

DETAILED DESCRIPTION OF THE PREFERRED EMBODIMENTS

Figure 12:
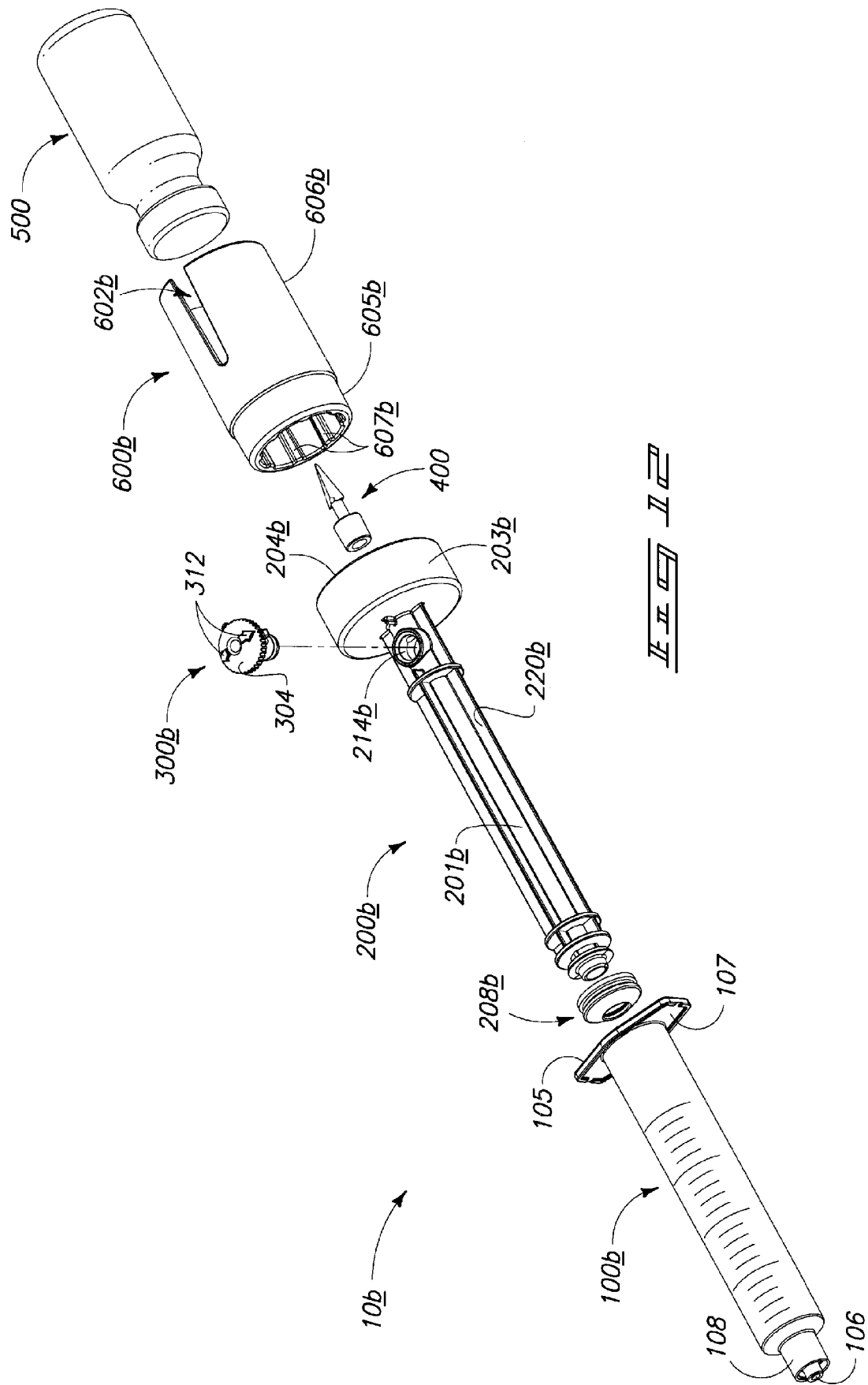
FIG. 12 is an exploded perspective view of a mixing assembly in accordance with another alternate aspect of the invention.

This disclosure of the invention is submitted in furtherance of the constitutional purposes of the U.S. Patent Laws "to promote the progress of science and useful arts" (Article 1, Section 8).

In general, the invention provides methodology for combining and mixing to produce a mixture and encompasses device configurations to allow combination and mixing of components. In particular, methodology of the invention involves combining and mixing components to produce an administration-ready agent such as a medicant and, in particular aspects, includes administering such agent to an individual. Accordingly, device configurations of the invention allow combination of separate components such that the combined and mixed components are administration-ready. In particular aspects the encompassed devices are additionally configured for use during administration of the administration-ready agent. The general concepts and exemplary devices in accordance with the invention are illustrated in the accompanying FIGS. 1-22.

Where devices in accordance with the invention are used for preparation of a medicant, the devices are preferably closed-system mixing assemblies. An exemplary mixing assembly 10 in accordance with the invention is illustrated in FIG. 1. The various components of the mixing assembly 10 are described generally with reference to FIG. 1 and will be described in greater detail with reference to subsequent figures. It is to be understood that the general features described with reference to FIG. 1 are exemplary and the invention encompasses modifications, alternate embodiments and adaptations including but not limited to those specifically illustrated in subsequent drawings.

Mixing assembly 10 can comprise a container such as a syringe body (or barrel) 100 and a piston 200 which has a fluid passageway passing entirely through the length of the piston (discussed further below). In some instances, a reversibly attached cap (not shown) may be present providing a fluid seal at a forward end of the syringe body. A valve 300 can be associated with piston 200 and can preferably be configured to allow selective fluid passage through the piston passageway. The mixing assembly can have an extension 600 which can comprise a cylindrical or alternatively shaped housing configured to receive a vial 500 or alternative second container within a chamber or opening within the extension. Assembly 10 can further comprise a puncturing device 400 associated with piston 200. Although FIG. 1 and subsequent figures depict assemblies as comprising syringes and the description presents methodology primarily in terms of preparing a medicant, it is to be understood that the invention encompasses alternative container shapes and adaptation of devices for use in mixing of components to form mixtures or agents other than medicants.

As illustrated in FIG. 1, a vial 500 which can be, for example, a standard medicant type vial, can be utilized and extension housing 600 can preferably be configured such that vial 500 is slideably insertable into an internal area of housing 600.

A mixing and administration system comprising mixing assembly 10 as illustrated in FIG. 1 can be described as being a closed-system in that separate components of an agent can be combined and mixed without exposing the components to an environment external to the mixing assembly. For example, a first component can be provided within vial 500 and a second component can be provided within syringe 100. Syringe 100 can be capped to retain the second component, with such cap being reversibly attached to allow removal as appropriate (described below).

As described in greater detail below, the fluid passageway through piston 200 preferably extends longitudinally and more preferably along the longitudinal axis from a first end of the piston stem through the piston and out a second end such that fluid communication can be established between vial 500 and the chamber of syringe 100. Accordingly, when valve 300 is positioned in an "open configuration" bi-directional fluid flow through the piston passageway is established allowing fluid communication between the syringe barrel (preferably capped) and vial 500.

Referring to FIG. 2, such shows an exploded view of the various general components of mixing assembly 10. Such view illustrates the general relationship of the various components, each of which is described independently in subsequent figures. Primarily it is noted with reference to FIG. 2 that piston 200 can comprise an independently fabricated seal or stopper portion 208 and that each of valve 300 and piercing structure 400 can be fabricated independently of the rod or stem portion of the piston. However, it is to be noted that the invention contemplates alternative aspects where one or more of stopper 208, valve 300 and piercing structure 400 are integral with the stem portion of the piston. It is to be additionally noted that extension 600 as depicted in FIG. 2 having an open end for receiving vial 500 can be fabricated to be independent of piston 200 as illustrated, or can be fabricated to be integral with the piston stem portion (not shown).

Referring to FIG. 3, syringe body 100 can comprise a cylindrical housing 102 having an interior region or chamber 104 within the housing. The chamber can be described as having a longitudinal axis extending from a first end 105 of the syringe body. A second end 106 of the syringe body is disposed opposing first end 105. In particular instances, the syringe can comprise a LUER-LOK® (Becton, Dickinson and Company, Corp., Franklin Lakes, N.J.) type fitting 108 disposed proximate the second end as illustrated in FIG. 3. Although a Luer-Lok, connector is illustrated it is to be understood that the invention contemplates alternative connector/fitting configurations. Preferably, connector 108 is able to receive and preferably reversibly receive a needle, alternative cannula, tubing and/or adaptors which can be utilized, for example, during administering of a medicant from within chamber 104 to an individual or in particular instances, for transferring into a distinct container (not shown). In particular applications it can be preferable that syringe body 100 comprise a male Luer-Lok type fitting to allow connection and preferably reversible connection with a female Luer-Lok fitting comprised by an administration needle.

Syringe housing 102 can have volume markings such as those illustrated, or can have alternative volume indicators to assist in measuring or verifying volume. Although not specifically illustrated in FIG. 3, a cap can be provided to seal second end 106 (see FIG. 19). The cap can prevent fluid passage from within the syringe barrel during storage, shipping, mixing, etc., and can prevent exposure of medicant components to an environment external to the syringe device. The cap can be configured to be reversibly attached by Luer-Lok or other fitting mechanism, to allow removal and replacement by an appropriate administration or transfer attachment.

Syringe body 100 can be a conventional type syringe barrel or can be manufactured for a particular application in accordance with the invention. The housing can be fabricated to comprise for example medical grade/approved glass or plastic material(s). Exemplary materials which can be utilized for syringe housing formation include but are not limited to polyethylenes, polypropylenes, polycycloolefins, polyvinyl chloride (PVC), polyamides (including aliphatic and aromatic variants), polyesters, polycarbonates, copolymer materials including but not limited to those containing ethylene-diene-propylene monomer (EPDM), polyacrylates, polyurethanes, composites, blends or combinations of such materials, or alternative composite materials.

The volume of the syringe (or alternate container) is not limited to a particular value and the syringe body can be configured to contain a maximum volume of, for example, from 1 ml to greater than 10 ml. Preferably the syringe volume will be less than or equal to 10 ml. For purposes of the present description, the syringe volume refers to the volume of liquid which the syringe housing is configured to retain and not the overall volume within internal region 104.

Referring next to FIG. 4, an exemplary piston 200 is illustrated having a stem portion 201, a first end 204 and a second end 202. The piston can be described as having a length represented by $d_1$ extending from first end 204 to second end 202. The length $d_1$ is not limited to a particular value and can preferably be a value greater than the length the longitudinal axis of internal syringe chamber 104.

A fluid pathway 206 traverses the length of the piston as illustrated by dashed lines. The diameter of fluid pathway 206 is represented in FIG. 4 by "$d_2$". In some instances pathway 206 can have a non-uniform diameter, however $d_2$ as used herein, indicates the minimum diameter of the passageway.

Although $d_1$ and $d_2$ are not limited to particular values, it can be preferable in some instances that the ratio of $d_1$ to $d_2$ be at least about 10:1. Capillary action can be promoted by maximization of the aspect ratio of passage length to diameter. Such capillary action can assist in creating an airlock within the passage when an associated valve is in a closed position, thereby avoiding contact of a liquid component/diluent, with the valve prior to opening of the valve at initiation of a mixing event (discussed below). However, smaller ratios can advantageously allow the entirety of the piston stem to be manufactured as a single piece by, for example, injection molding techniques. Accordingly the invention contemplates alternate $d_1$ to $d_2$ ratios (i.e. less than about 10:1).

As illustrated in FIG. 4, a stopper portion 208 can be provided to be received onto second end 202 of piston 201. In contrast with conventional syringe plungers, stopper portion 208 can be configured to have an opening or channel 210 passing entirely through the stopper allowing fluid passage from within passage 206 through stopper 208. Although a single channel 210 is depicted, the invention contemplates stopper configurations having a plurality of channels providing fluid passage through the stopper to/from the passage through the piston stem. As depicted in FIG. 1, piston 200 is configured such that second end 202 is receivable within the syringe chamber such that fluid communication can be established between the syringe chamber and piston passageway 206 through stopper 208 via opening(s) 210 as illustrated in FIG. 4.

Where stopper 208 is formed as an independent structure relative to the piston stem, the stopper can preferably comprise a relatively soft material (with respect to the piston, discussed below). Exemplary materials which can be appropriate for fabrication of the stopper based upon manufacturability, biocompatibility and/or chemical compatibility, and ability to produce a fluid seal include elastomeric materials such as rubber, butyl, silicones, silanes, polypropylene, polypropylene-EPDM, polyurethanes, and other appropriate plastics, as well as various copolymers, blends and combinations thereof.

Referring again to FIG. 4, piston 210 can additionally comprise various supporting rings 212, 216 and 217. It is to be understood that such rings are an optional feature and that stem portion 201 can be fabricated to comprise fewer rings than that depicted, to comprise none of the rings depicted, or to comprise additional rings relative to those depicted. The ring structures can additionally be alternately positioned along the piston stem relative to the positioning shown. In embodiments wherein stopper 208 is an independently formed structure, at least two of rings 212 are provided for mounting, positioning and retaining the stopper upon the piston. Ring structures 212, 216 and 217 can be advantageous, for example, for stabilizing and/or maneuvering piston 200 and to assist in reducing or avoiding contamination of internal syringe body surfaces during syringe manipulation, especially for embodiments where packaging is removed prior to manipulation of the mixing assembly (discussed below).

As additionally illustrated in FIG. 4, piston 200 can comprise an opening 214 extending through piston stem 201. Such opening can preferably orthogonally intersect fluid passageway 206. Such opening can be configured to allow insertion of a valve such as the exemplary valve depicted in FIG. 5. The depicted positioning of opening 214 along the length of piston stem 201 of FIG. 4 is exemplary. The positioning of valve opening 214 is not limited to any particular location and can be anywhere along the length of fluid path 206. It can be preferable in some instances that valve insertion opening 214 be positioned at the halfway point along distance $d_1$, or alternately to be more proximate end 204 than to end 202. This positioning can advantageously allow ease of manipulation of the associated valve.

As depicted in FIG. 1 assembly 10 can be configured such that valve 300 is, when disposed in association with opening 214, at least partially insertable within syringe housing 100. However the invention contemplates positioning of valve 300 more proximate end 204 than that depicted, especially for small volume syringes where a valve such as exemplary valve 300 shown is too large to fit insertably within the syringe housing. It is to be understood that alternative valve types can be utilized which can allow insertion or partial insertion of the valve into the syringe housing even for very small volume syringes.

Exemplary valve 300 is shown in greater detail in FIG. 5. As illustrated, valve 300 has a body portion 302 and a head portion 304. Head portion 304 can be configured to have extension or protrusion tabs 307 and 308. Although FIG. 5 depicts two extension tabs it is to be understood that fewer or greater than two extension tabs can be utilized. Extension tabs 307 and 308 can advantageously assist proper positioning and alignment of a fluid passageway 306 which passes through stem portion 302 of valve 300. The invention additionally contemplates alternative shapes for head portion 304 relative to the round configuration depicted. For example, the head portion can be arrow-shape to allow visual and/or tactile indication of valve position. Head portion 304 can also be configured to have alternative or additional visual and/or tactile indicators.

Valve body 302 is preferably configured to allow insertion of such portion into, and in particular instances entirely through, opening 214 of piston 200 as illustrated in FIG. 4. Accordingly, and as illustrated in FIG. 5, one or more seal or o-ring 310 can be provided to provide a fluid seal within opening 214. Alternatively, a seal can be formed as an integral part of valve body 302 (not shown). Although opening 214 and the associated valve 300 are illustrated as being configured such that the valve passes entirely through piston stem 201, it is to be understood that the invention contemplates alternative configurations where opening 214 and an associated valve, span less than an entirety of the cross-section of piston stem 201 (not shown). Additionally, although FIG. 5 shows a two-way (on/off) stopcock type valve, the invention contemplates alternative valve types and appropriate opening configurations. For example, rather than the uniform-diameter cylindrical valve opening depicted, opening 214 can be configured to be conical, rectangular, or other shape. In such instances, valve body 302 can be appropriately shaped to be received within the opening. Alternative valve types such as bidirectional stop valves, slider-type valves, ball valves, push valves, or gate valves can be utilized and can be appropriately configured based upon the dimensions of opening 214.

In addition to the single piece piston stem 201 illustrated in FIG. 4 the invention contemplates utilization of multipart piston stems. Referring to FIG. 6, an exemplary two part piston stem 201 is illustrated having a first portion 230 and a second portion 232. In the exemplary two-part piston stem illustrated parts 230 and 232 interface at the longitudinal position of opening 214 along the piston axis. Parts 230 and 232 can be joined by, for example, thermal welding, ultrasonic welding, radio-frequency welding, adhesive bonding or other appropriate bonding techniques. Alternatively, the two portions can be configured to snap together or can be secured by various joining structures such pins, clevises, threads or alternative mechanical attachment techniques known in the art or yet to be developed.

Although the two part piston stem illustrated depicts an interface between the two parts coinciding with the position of valve receiving opening 214 it is to be understood that the positioning of the interface is not limited to any particular location and can be, for example, anywhere along the longitudinal length of the piston stem. Appropriate positioning of the interface and length of the resulting segments can be adapted as appropriate based on ease of manufacture of an appropriate valve and piston segments. The invention additionally contemplates multi-part piston stems having more than two independently manufactured segments (not shown).

The piston and the syringe housing portions of the devices of the invention can typically comprise standard materials utilized for conventional syringe and piston/plunger formation. Typically, the piston, exclusive of the stopper, will be a relatively hard plastic. In embodiments where the stopper is integral with the piston, the integrated piece may be formed of a common plastic material. Exemplary plastics which can be utilized for piston formation include but are not limited to polyethylenes, polypropylenes, polycycloolefins, polyvinyl chloride (PVC), polyamides (including aliphatic and aromatic variants), polyesters, polycarbonates, polyacrylates, polyurethanes, copolymers, blends, composites, and combinations thereof.

Valve 300 is also not limited to a particular material and can preferably comprise plastic and/or elastomeric materials. In particular applications it can be preferable that valve body portion 302 (as illustrated in FIG. 5) comprises an elastomeric material to allow a better fit and/or seal within the opening 214 of piston stem 201, especially where piston 200 comprises a hard plastic material. Exemplary elastomeric materials which can be utilized for body portion 302 include but are not limited to polyurethanes, polypropylene-EPDM, other polypropylenes, polysiloxane and/or silicone materials, butyl materials, isoprenes, neoprenes, polyethylenes, and various copolymers, composites, blends or other combinations of such materials. Additional appropriate materials may include natural rubbers, nitrile rubbers and combinations thereof. Valve 300, exclusive of o-ring 310, can be constructed as a single piece and therefore can be formed of a particular material or type of material. Alternately, head portion 304 can be formed independently and comprise a material that differs from body portion 302. For example, in particular instances head portion 304 can be formed of a hard plastic such as any of those listed above and body portion 302 can comprise either a distinct hard plastic material or any of the elastomeric materials listed above.

Referring to FIG. 7, such shows an exemplary piercing structure 400 in accordance with the invention. Piercing structure 400 can be described as having a head segment 401 comprising a tip 402 disposed at a first end. Piercing structure 400 additionally has a stem/body portion 403 extending from head portion 401 to a base surface 404 disposed at a second end of the structure opposing the first end. A channel 406 or other fluid passageway extends through the base surface and preferably through an entirety of body portion 403.

The piercing structure 400 shown in 406 illustrates an exemplary shape and form of head segment 401. As illustrated, head portion 401 can have an external surface comprising a front surface 414 (or upper surface as illustrated) and an opposing back surface 415. In a preferred aspect of the invention channel 406 extends less than an entirety of an internal length of head segment 401 such that the channel does not pass through tip 402. Rather, one or more access holes 408 are provided, for example, through one or both of surfaces 414 and 415. Such configuration where the channel does not pass through the tip can advantageously minimize or prevent coring of the septum material or plugging of the channel during a piercing operation.

Access holes 108 can be disposed orthogonal relative to the longitudinal axis of channel 406 as depicted in FIG. 7 or can intersect channel 406 at an angle of other than 90° (not shown). Additionally, the placement of holes 408 along head segment 401 is not limited to the position shown. It can be advantageous for holes 408 to be disposed proximate the body portion of the piercing device to allow such holes to lie just within a vial upon piercing. Such can maximize fluid access allowing efficient and complete extraction of vial contents without repositioning of the piercing structure after piercing of a septum or other barrier material.

To assist in puncturing and passing of head segment 401 through a punctured material such as, for example, a septum, head portion 401 can be configured to have one or more edges 410 and 412 be cutting edges, where the term "cutting edge" refers to an edge having a sharpness sufficient to cut the material being pierced during a piercing operation. As illustrated in FIG. 7, cutting edges 410 and 412 can preferably be disposed at the edges of head portion 401 where surfaces 414 and 415 meet. Although the figure illustrates two cutting edges it is to be understood that the invention contemplates configurations of head portions 401 which have no cutting edges, one cutting edge or more than two cutting edges. As further illustrated, one or both of surfaces 414 and 415 can be beveled. Such surface beveling can additionally aid in passing of head segment 401 through a punctured material.

Body portion 403 of piercing structure 400 can be, for example, cylindrical as illustrated in FIG. 7. Body portion 403 can have a uniform circumference throughout its length (not shown) or can have segments which vary in circumference relative to one another. For example, as illustrated in FIG. 7 body portion 403 can have a tube segment 416 and a base segment 418 where base segment 418 extends from base surface 404 to tube segment 416. The lengths of segments 418 and 416 are not limited to any particular values. Nor is the ratio of segment lengths limited to a particular value. Preferably, where base portion 418 will be seated within another component of a mixing assembly in accordance with the invention (such as piston 200), the length of segment 418 can be such to allow stabilization and/or retention of piercing structure 400 in the seated position.

Base portion 418 is preferably of sufficient length and appropriate shape to be securely seated within a seating opening comprised by the piston (see below). An o-ring or raised portion of base 418 (not shown) can be provided to allow a tight fitting. Accordingly, an appropriate indentation or groove (not shown) can be provided within the seat opening of the piston. In particular instances, a press fit or friction fit will be utilized for providing sufficient retention of the piercing structure. Secure joining may optionally be utilized utilizing for example, an adhesive, welding, or other appropriate joining technique.

With respect to segment 416, such can preferably be of sufficient length to pass entirely through a punctured material to allow fluid passage across the punctured material via access hole 408 and through passageway 406. Accordingly, an appropriate length of segment 416 can be determined by the thickness of a septum or other barrier to be punctured, while positioning access hole 408 as near the punctured material as possible to allow maximum fluid access (discussed above). Further, although the piercing device is not limited to a particular shape, the "arrowhead" shape configuration depicted in FIG. 7, where head segment 401 has ridge surfaces 409 which extend laterally outward relative to tube segment 416, can assist in stabilizing and retaining the piercing device across a septum after puncturing has occurred. Retention of the piercing device across the septum can avoid inadvertent contact of the device by an individual which could cause injury and/or contamination of the medicant.

Numerous appropriate materials are available for fabrication of piercing device 400. Such materials include but are not limited to metals, such as stainless steel, and various plastics such as polyamides, polyacrylates, polycarbonates, epoxies, polyurethanes, polysulfones, polytherimides, polypropylenes, copolymers, etc., in either thermoplastic or thermoset varieties.

In addition to the piercing structure depicted in FIG. 7, and variations of such configuration, the invention contemplates utilization of alternate structures to puncture a container barrier. Piston 200 can be adapted accordingly. Alternate structures can include, for example, a needle or a non-coring piercing structure of alternative shape relative to the arrowhead design depicted. Such alternative configurations can be especially useful where multiple vials are to be accessed sequentially (i.e. during preparation of a medicant comprising three or more components).

An exemplary vial 500 which can be utilized as part of a mixing assembly in accordance with the invention is illustrated in FIG. 8. For purposes of the invention, the term "vial" is not limited to a particular container structure and can be used to refer to various containers including containers utilized for parenteral as well as non-parenteral materials. Vial 500 can be, for example, a bottle such as illustrated in FIG. 8 having a cap portion 504 and an upper surface 502. Vial 500 can be a glass bottle or alternatively can be a plastic container or other material utilized conventionally or yet to be developed for retaining and/or accessing a medicant or component thereof.

Referring to FIG. 9, such shows and exemplary engagement configuration of piercing structure 400 and vial 500. In the illustration of engagement, devise 400 is illustrated as passing through a septum 506 within cap portion 504 of vial 500. Accordingly, fluid access is provided from within vial 500 through access hole 408 into and through fluid passageway 406.

An exemplary association of puncturing device 400 and a piston 200 in accordance with the invention is shown in FIG. 10. As illustrated, base portion 418 (shown in FIG. 9) of the puncturing device is seated within a terminal portion of passageway 206 of piston stem 201. Such terminal portion can preferably be diametrically enlarged relative to other portions of passageway 206 to allow seating of the piercing structure. FIG. 10 additionally illustrates an exemplary fitting 203 and ridge 205 present at the first end 204 of the piston structure. As illustrated, fitting 203 can have an interior area 207 having a base surface 213 with puncturing device 400 passing through such interior area and base surface. Although base surface 213 is illustrated as being flat, the invention contemplates seating configurations where a central portion of base surface 213 is raised within area 207 to form a pedestal or boss (not shown), where a central opening within the raised portion is an extension of the fluid passageway through the piston and is configured for seating the puncturing device. It can be advantageous to provide a raised portion to provide a space between base surface 213 and the top of vial 500. The raised boss configuration can be adjusted to allow proper fitting and/or positioning of a particular vial within the receiving housing and association with the puncturing device.

Interior area 207 can be of sufficient size to allow a portion of a vial or container, such as cap portion 504 illustrated in FIGS. 8 and 9 to be at least partially insertable within the fitting 203. Additionally, fitting 203 can have an outer diameter of an appropriate size to allow insertion of fitting 203 within an extension structure (such as the cylindrical housing extension structure shown in FIGS. 1 and 2). Where fitting 203 is configured for insertion within an extension structure, ridge 205 can preferably be configured to interface with the extension structure to allow an appropriate positioning of the extension structure relative to piston 200 as illustrated in FIG. 1 for example.

Referring again to FIG. 1, a general methodology in accordance with the invention for the illustrated embodiment can comprise mixing a first component provided within vial 500 with a second component provided within syringe barrel 100. In an initial state prior to the combining of the two components, each component is isolated from the other. Piston 200 is preferably provided in an initial position relative to the syringe barrel with valve 300 being initially disposed in an "off" position, blocking fluid passageway through the piston.

In the initial state, syringe 100 is preferably capped or otherwise sealed (not shown) to prohibit passage of material into or out of syringe barrel 100 through the second end of the syringe. Piston 200 is initially disposed in an inserted position through the first end of syringe barrel 100 and positioned to allow containment of the second component within the syringe barrel. Stopper 208 (illustrated in FIG. 2) preferably prohibits passage of the component from within the syringe barrel between the internal surfaces of the housing and the stopper.

While valve 300 is in the off position, vial 500 is positioned by partial insertion within extension housing 600. It is to be noted that such insertion can, in alternate aspects, be performed by an end user of the mixing assembly or can be performed prior to packaging of the assembly (discussed below). Regardless, the vial cap/septum is initially provided to be intact and preferably to be spaced from puncture device 400 such that the tip of the puncture device is not in physical contact with any portion of vial 500 as initially provided.

Once combination and mixing of the separate components is desired, vial 500 can be repositioned by, for example, sliding vial 500 farther within extension 600 to allow device 400 to puncture and be partially inserted through the septum or alternate barrier portion of the vial.

Once puncturing has occurred, valve 300 can be rotated or otherwise repositioned into an open position allowing fluid passage through the piston. Such repositioning establishes fluid communication between the interior of vial 500 and the interior of syringe barrel 100 without exposing either of the two components to an environment external to the mixing assembly. One or both of the first component and second component can preferably be in liquid form. Typically, at least the component within the syringe barrel will be in liquid form. Often, the component within vial 500 will be in a dry, powdered or lyophilized form, but may alternatively be in the form of a liquid, solution, suspension or other mixture.

Where vial 500 contains a non-fluid component, a liquid component contained within syringe 100 can be introduced into vial 500 and can be combined with the component within vial 500 by, for example, sliding piston 200 from an initial position to a second position such that stopper 208 is repositioned to be nearer the second end of syringe body 100. Such sliding motion allows fluid to flow from within the syringe chamber through piston 200 and into vial 500 via valve 300. During the passage the fluid additionally passes through puncturing device 400.

Mixing of the combined components can be performed by, for example, a forward and reverse sliding motion of piston 200 relative to the syringe barrel in a "pumping" type motion. The pumping motion is conducted with the valve 300 in the open position allowing fluid communication between the syringe barrel and vial 500, typically with the vial being in an inverted position. Alternatively, mixing can be conducted by shaking or agitation of vial 500 and/or the entire mixing assembly, or by a combination of pumping action and shaking, agitating, etc. Once the components have been mixed, the assembly can be prepared for transfer of the mixed agent or, where the mixture is an administration-ready agent the device can be prepared for administrating the agent to an individual. Alternatively, if additional components are to be combined with the mixture, such can be introduced by, for example, flowing into the syringe via the second end, and mixing as described above.

In order to prepare for transfer and/or administration of the agent, the mixture, can be drawn into syringe body 100 by, for example, sliding piston 200 in a rearward motion, typically with the vial in an inverted position. In other words, piston 200 is partially extracted moving stopper 208 toward the first end of the syringe housing. Upon drawing of all or an appropriate measured amount of the mixture into the syringe barrel, valve 300 can be rotated or otherwise repositioned into the closed position blocking fluid passageway from the syringe barrel through the piston. The syringe barrel can then be uncapped by, for example, removal of a cap such as Luer-lok cap fitting. It is to be understood that the invention also contemplates performing the mixing/preparation of the medicant with a needle fitted to the Luer-lok fitting during the preparation stage. However, the needle is preferably capped and sealed during such operation or otherwise prevented from allowing passage or exposure of material from the syringe barrel to an environment external to the assembly.

Where a cap is removed in preparation for transfer or administration of the agent, an appropriate transfer device such as a needle, cannula, transfer tube and/or other appropriate fitting can be attached to the Luer-lok connection and transfer/administration can occur by sliding forward of the piston within the barrel, thereby expelling the contents of the barrel through the needle or alternate transfer structure at the Luer-lok end of the syringe. Such transfer is performed with valve 300 remaining in the closed position throughout. Alternatively, transfer can be accomplished by providing assembly 10 into an appropriate syringe pump, as will be understood by those skilled in the art.

Referring next to FIG. 11, such shows alternate aspects of the invention having variation relative to the mixing assembly shown in FIGS. 1-10. Components that vary relative to those illustrated in earlier figures are either given numeric identifiers having a appendant "a" or a unique identifier relative to those used previously. In the embodiment shown in FIG. 11, piston portion 200a is shown as having lateral rib structures 220a extending lengthwise along stem potion 201a. Such rib features can be similar or identical to those present on conventional syringe plunger devices. The presence of ribs 220a can provide additional support and thereby strengthen the piston. As illustrated, ring structures 212a, 216a are present at various positions along the length of the stem portion. It is to be understood that the invention contemplates alternate placement and/or alternate numbers of both ring structures and ribs relative to the exemplary configuration depicted in FIG. 11.

As shown in FIG. 11, one or more of rib structures 220a can be provided to be gapped in the region of valve receiving opening 214a. The width of the gap can be configured to allow sufficient space for insertion of the valve and to allow positioning of the head portion of the valve within the gap. It is noted that the extension tabs present on the head of the valve can be specifically configured to come into contact with a rib upon rotation of the valve head. Such can advantageously allow proper open/closed positioning of the valve and alignment of the fluid passageway through the valve and piston stem 201a.

Mixing assembly 10a as shown in FIG. 11 utilizes an extension portion 600 having a groove 602 extending partially along the length of the extension housing. Extension portion 600 can comprise two grooves as illustrated or can comprise fewer or greater number of grooves. Such grooves can allow a slight expansion in the interior circumference of the extension housing. This feature can allow a tight yet reversible fit to be established between extension housing 600 and vial 500. For example, where the internal area 604 of the extension has a circumference which is slightly less than or equal to the maximum circumference of vial 500, grooves 602 can allow a slight expansion of the housing to allow insertion of vial 500. Such configuration can additionally allow retention of vial 500 within internal region 604 until force is applied to extract the vial.

The length of the groove(s) 602 can be configured to allow positioning and stabilization of vial 500 within the housing in a position which disposes a septum or cap of vial 500 in a spaced relationship relative to puncture device 400 (discussed below). The spaced relationship can allow packaging and/or shipping of an assembly as a linearly assembled device where the cap of vial 500 remains intact prior to removal of some or all of packaging materials and/or intentional engagement. Accordingly, the length of grooves 602 and the relative length of the grooves and the overall length of housing 600 can vary with appropriate lengths and length ratios depending upon the relative length and positioning of device 400 within such housing and the relative size of vial 500.

An additional alternative aspect of the invention is described with reference to FIGS. 12-13. Referring initially to FIG. 12, such shows variation of the components of mixing assembly 10b relative to the mixing assemblies described in previous figures. Components that vary relative to those illustrated in earlier figures are given either a numeric identifier having an appendant "b", or a unique identifier relative to those previously used. In the embodiment depicted in FIG. 12, piston portion 200b is shown as having an alternative fitting 203b configuration. Such configuration can allow a portion of extension housing 600b to be received within an internal area of fitting 203b. As illustrated by the exploded view, puncturing device 400 can be seated within piston 200b in a manner similar to that described above with respect to earlier embodiments. Additionally the various rings and fins depicted in FIG. 12 in association with piston 200b can be as illustrated or can have any of the alternative configurations described above.

Valve 300b as depicted in FIG. 12 can comprise one or more alignment markers 312 preferably on an upper surface of valve head 304 to allow visible and/or tactile alignment of the valve upon insertion within opening 214b of piston 200b. Although depicted as molded arrows, it is to be understood that the invention contemplates alternative alignment markers.

The extension 600b shown in FIG. 12 illustrates aspects of the invention where the extension housing has a non-uniform outer circumference. As shown, extension housing 600b can comprise a first portion 605b having a smaller circumference than a second portion 606b. Such configuration can allow insertion and seating of portion 605b within the piston fitting configuration 203b as illustrated.

Figure 13A:
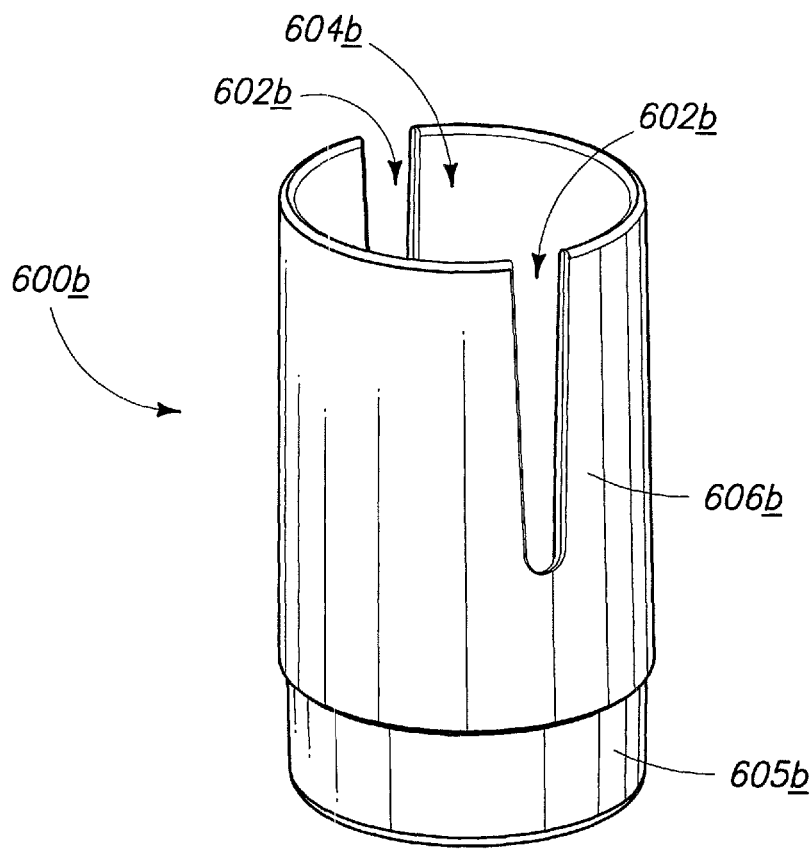
FIG. 13 illustrates an extension housing from a perspective view (Panel A) and an end view (Panel B) in accordance with the aspect shown in FIG. 12.

The features of extension 600b are described and more fully illustrated with reference to FIGS. 13A and B. As shown in FIG. 13A, extension housing 600b has an internal area 604b configured to receive a vial such as a standard vial or an alternative container as described above. One or more slots 602b can extend longitudinally from the receiving end of the extension housing to allow slight expansion of the housing. In some instances, the receiving/opening end of housing 600b can have an internal diameter equal to or slightly smaller than the diameter of a vial prior to insertion of the vial. Insertion of the vial can expand the housing due to the presence of slots 602b. Such configuration can allow a snug fit and stabilization of the inserted vial. In combination with particular packaging aspects (discussed below) slots 602b can additionally, allow stabilization of vial positioning during storage and/or shipping.

Figure 13B:
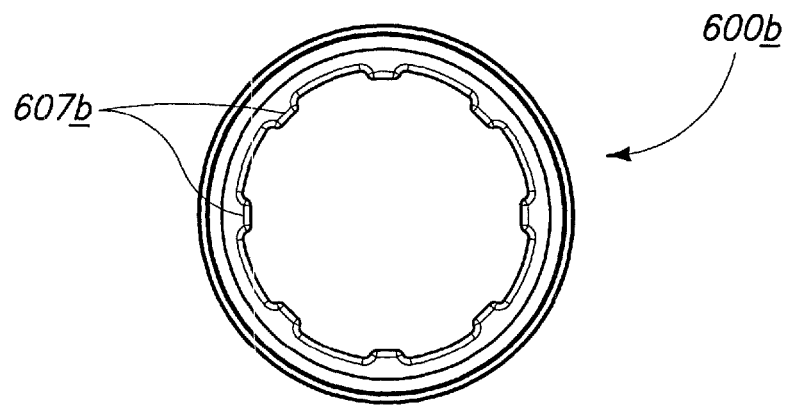

Referring to FIG. 13B, at least a portion of a length of the interior area can comprise interior ribs 607b. Preferably, at least an interior length associated with segment 605b contains ribs 607b which can assist in positioning and retaining vial 500 (shown in FIG. 12) within the extension housing. Such ribs can additionally provide support for the vial within the housing upon puncturing of a septum or alternative barrier material.

Although FIG. 13 depicts extension 600b as having ribs 607 along only a portion of interior sidewalls of opening 604b, it is to be understood that the invention contemplates alternative aspects where ribs are provided along a portion or an entirety of the interior surface of segment 606b. The interior sidewalls and/or rib portions within housing 600b can be contoured to correspond to an outer shape of vial 500 whether the vial is of the conventional shape illustrated or has and alternative vial or container shape.

Although housing configurations having segments of non-equivalent circumference are illustrated in FIG. 12 as being utilized with a single piece piston stem, it is to be understood that the invention contemplates utilization of such housing configuration with any of the alternative piston configurations described herein.

Figure 14:
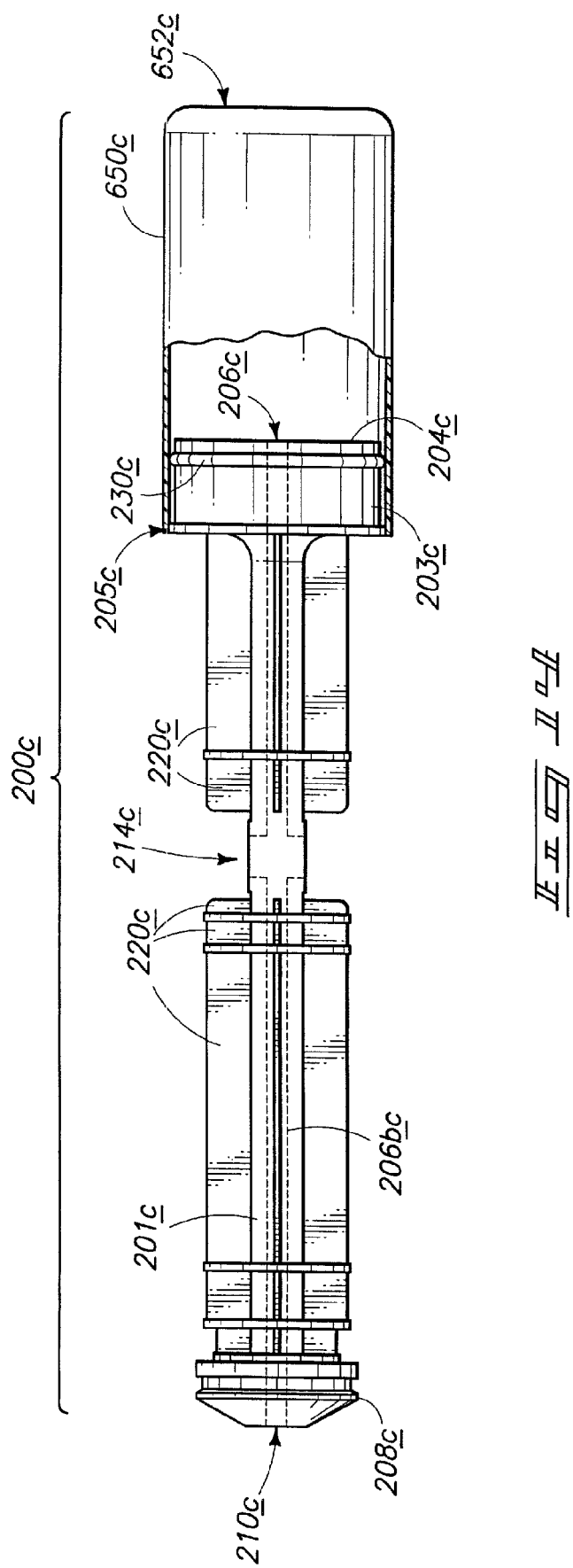
FIG. 14 shows a side view of a mixing device having an integral housing configuration in accordance with one aspect of the invention.

In addition to the embodiments described above wherein vial 500 is provided independently of the piston portion of the assembly the invention additionally encompasses configurations where a container is integral with the piston portion as exemplified in FIG. 14. The exemplary piston 200c has features having numeric identifiers with an appendant "c" to distinguish from earlier embodiments. It is to be noted, however, that the general concepts and variations of the earlier embodiments can apply equally to the embodiment depicted in FIG. 14. It is to be additionally noted that in the piston 200c, stopper portion can be provided as an independent component or can be an integral part of piston 200c. Accordingly, stopper 208c can comprise a material that differs from the piston stem or can be formed of a material identical to the material utilized for forming piston stem 201c.

The alternate aspects of the invention depicted in FIG. 14 include variation of the extension portion to form a container 650c having a base surface 652c which opposes first end 204c of the piston forming an enclosed compartment. Container 650c can be formed to be integral with the piston during a common fabrication event (such as molding), or by affixing an independently formed container structure to the fitting portion 203c of the piston. Alternatively, container portion 650c can be reversibly attached to the piston. Attachment (whether permanent or reversible) of an independently formed container to second end 204c can comprise insertion of fitting portion 203c similar to the attachment of extension portion 600 described above. Joining and affixing of the container portion to the piston can comprise for example a snap-on type joint or welding.

Alternative integral vial-piston configurations contemplated by the invention include, for example, providing an opening through the vial portion, for example through base surface 652c (not shown), which can be utilized during providing of a medicant component into the vial and/or during drying or lyophilization of the component. Such opening can be subsequently capped or otherwise sealed.

The material utilized for construction of container 650c is not limited to a particular or class of materials. Container 650c can in particular instances be formed of a plastic material which can be either a rigid material or a collapsible material.

A component of a medicant or other mixture to be formed can be provided within container 650c and can be isolated from an associated syringe barrel (not shown) by providing a valve into valve receiving opening 214c. An appropriate valve can be, for example, any of the valves described above. The component provided in container 650c can be provided within the container prior to attachment of the container or alternatively can be provided into the integral or attached container via fluid pathway 206 through the piston and stopper opening 210c. The associated valve can then be closed to prevent the contained component from flowing outward through the piston.

Where container 650c is formed independently and is attached to the piston either reversibly or permanently, an o-ring 230c can be provided in association with fitting 203c to provide a fluid seal between the piston and internal surfaces of container 650c. Alternatively, other appropriate sealing techniques can be utilized. It is noted that piston 200c lacks an associated piercing structure. Accordingly, first end 204c of the piston can be modified from earlier discussed configurations to lack accommodation features for the piercing device. Further, the illustrated attachment of container 650c to piston 200c is an exemplary configuration and alternative shapes and attachment methods are contemplated.

Although the integral container/piston structure illustrated is shown to have rings and ribs 220c it is to be understood that the ribs and rings are optional as is the number of such ribs and/or rings, as set for above with respect to earlier described aspects. Additionally, piston stem 201c, which is shown as a single piece, can alternatively comprise multiple segments as described above (and/or the rotational valve type configuration described below).

Another alternate piston configuration involving a rotational-valve type piston is exemplified and described with reference to FIGS. 15A-D. Referring initially to FIG. 15A, a piston 200d is depicted which can be utilized in conjunction with additional mixing assembly components discussed above. Piston 200d can comprise a two part piston stem 201d which can optionally include ribs 220d and/or rings 212d. Stem 201d comprises a first portion 230d and a second portion 232d. The lengths of first segment 230d and second segment 232d can be identical or can differ. The length of each segment and their relative lengths thereof can be determined by manufacturability and overall length of the piston. Piston 200d is shown as having an independently formed stopper 208d. However, it is to be understood that such stopper can be integral with first portion 230d of piston 200d. An exemplary extension portion 600d is illustrated which can be configured for receiving a vial as described above. As illustrated in FIG. 15, extension portion 600d can be integral with second portion 232d. Such integral piston/extension configuration can be adapted for use with any of the alternative single part piston stem aspects described.

Referring next to FIG. 15B, such figure shows an exemplary puncturing device 400d which can be disposed within an internal region of extension 600d and which can be positioned to allow communication between an associated vial and fluid pathway 206d which traverses the length of piston stem 201d. First segment 230d and second segment 232d can be configured to interact to provide valve action. As illustrated, first segment 230d can comprise a frustoconical protrusion 226 having a pair of openings 228 which pass entirely through the frustoconical protrusion. Second portion 232d can be configured to have a corresponding frustoconical interior chamber region 227 configured to receive protrusion 226. Although a frustoconical shape is illustrated, the invention contemplates protrusion shapes and corresponding receiving chamber shapes other than the exemplary frustoconical shape.

Fluid passageway 206d is shown as extending partially through frustoconical protrusion 226 in a discontinuous manner such that direct longitudinal fluid passage is prevented. Fluid passage 206d resumes its longitudinal progress on an opposite side of a solid block of material 223. One or more grooves 229 can be disposed within an interior sidewall of second segment 232d which, when aligned with openings 228 can allow fluid passage from fluid passageway 206d of first portion 230d into the portion of such fluid passageway passing through second portion 232d. Alignment of openings 228 with grooves 229 can be achieved by opposing rotation of portion 230d relative to portion 232d. Such valve/piston configuration is further described with reference to FIG. 15C. As illustrated, protrusion 226 can comprise one or more O-rings 222 to allow fluid seal to be formed upon insertion of the protrusion into receiving chamber 227.

Referring to second segment 232d of piston 200d, a pair of grooves 229 is illustrated as being arc shaped grooves formed in the sidewall material of the piston. It is to be understood that alternative shaped grooves are contemplated and the arc shaped grooves are but one exemplary configuration. Referring next to FIG. 15D, upon insertion of the protrusion into the receiving chamber of second segment 232d, rotation of part 230d and 232d relative to one another can be performed to align fluid access openings 228 with grooves 229 to allow connection of passageway 206 via access openings 228 allowing fluid passageway between segments 230d and 232d. Further rotation or reverse rotation can be utilized to misalign access openings 228 and groove 229 to again close fluid access between the two piston parts.

Although fluid access openings 228. are shown as extending entirely through protrusion 226 (see FIG. 15C) it is to be understood that such openings can extend less than an entirety of the width of such protrusion. Alternatively, access openings 228 can be provided on a single side of such protrusion. In another alternative, additional access openings can be provided partially or entirely through protrusion 226. Similarly, a fewer or greater number than the illustrated two connecting grooves can be provided within second segment 232d.

In addition to the features shown and described above, in particular instances one or more filters may be utilized for removal of particulates prior to administration. Appropriate filter(s) may be incorporated within any of the devices above for example within the fluid passageway through the piston. Additionally or alternatively, one or more filters may be provided in association with the syringe outlet, either internally or externally to the syringe barrel.

Methodology for mixing components to prepare a mixture utilizing the rotational piston type valve configuration illustrated in FIGS. 13A-D can be conducted in a manner similar to methodology described with reference to FIG. 1. Using the rotational piston type device, rather than rotating or repositioning independent valve component 300 illustrated in FIG. 1, first and second segments of the piston would be opposingly rotated to open or close fluid passageway through the piston at the appropriate stage of the mixing procedure.

Figures 16A, 16B:
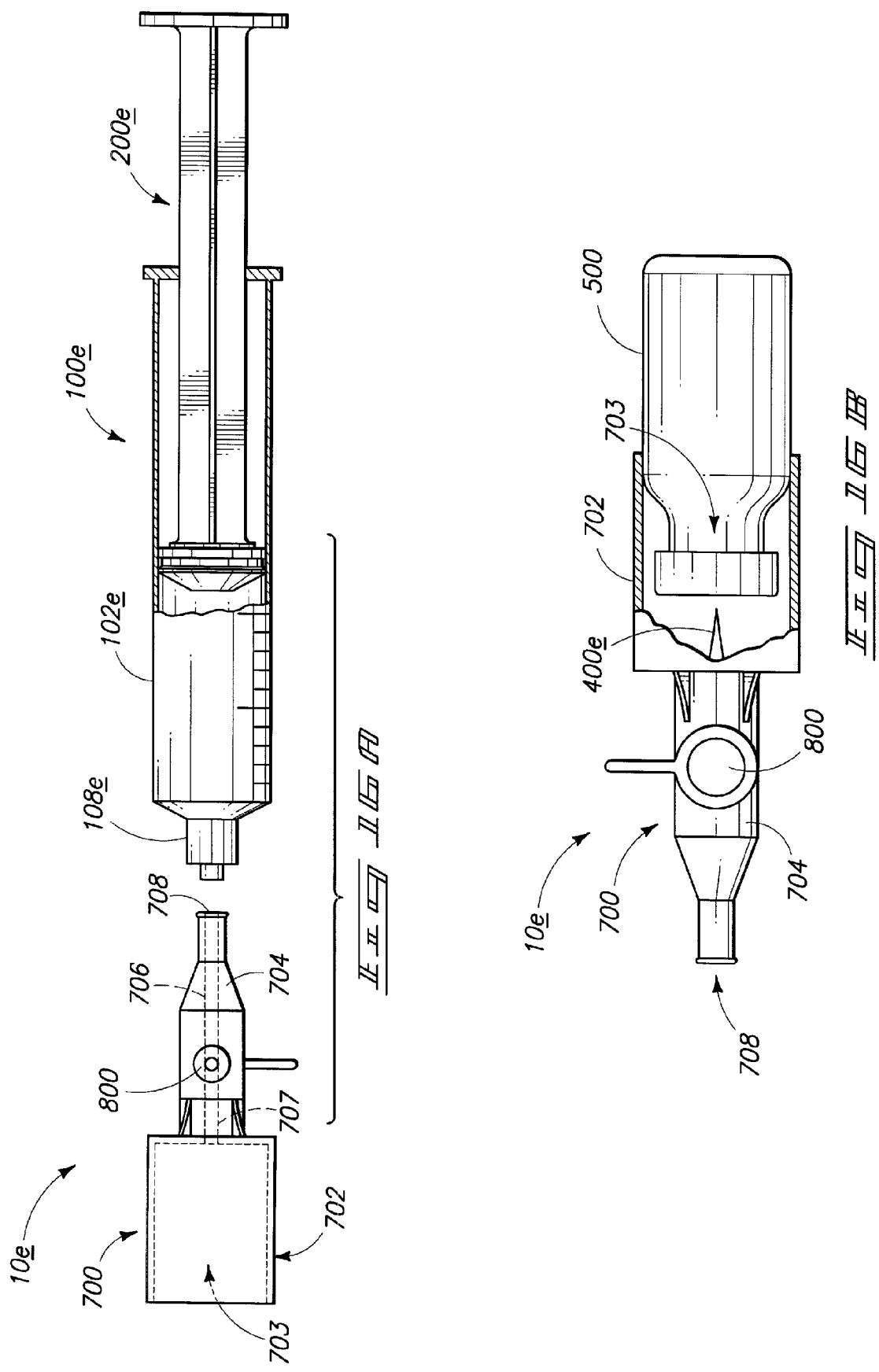
FIG. 16A is a side view and partial cross-sectional view of a mixing assembly in accordance with an alternative aspect of the invention.
FIG. 16B is a side and partially cross-sectional view of an adapter portion of the assembly shown in FIG. 16A shown in association with an exemplary vial.

Another alternate embodiment of a mixing device in accordance with the invention is described with reference to FIGS. 16A-B. Referring to FIG. 16A, a mixing system 10e can comprise a syringe 100 and an adapter 700 which can be reversibly attachable to the syringe 100 by, for example, providing a female Luer-lok or alternative fitting 708 on a first end of adapter 700. Syringe 100 can preferably be a conventional syringe utilizing a conventional type piston/plunger 200e. Adapter 700 can be provided to have a first fluid passageway 706 (denoted with dashed lines) which passes through female Luer-lok fitting 708 and through a segment of adaptor housing 704 to a valve 800, and a second fluid passageway segment 707 (denoted with dashed lines) which passes from the valve 800 to an interior area 703 of a vial housing 702. Although depicted as inline passageways, the invention contemplates passageways 706 and 707 being angled or orthogonal relative to one another.

As illustrated in FIG. 16B, internal chamber 703 can be configured to receive a vial 500 such as, for example, a standard vial. Alternative vials or container types can be utilized as described above. Vial housing 702 can additionally be configured to contain an associated puncture device 400e which can be similar to or identical to the puncture devices described above. Insertion of vial 500 into housing 702 can be as described above with respect to extension housing 600 with reference to FIGS. 1-10.

Adapter 700 can be formed of any appropriate material and in particular instances will comprise a plastic material such as any of the plastic materials discussed above with respect to syringe housings and pistons. Valve 800 can be any of the valve types discussed above with respect to exemplary valve 300 and can accordingly comprise any of the materials described with reference to such exemplary valve. Alternatively, adapter 700 can be configured to have a rotating type valve system as discussed with reference to FIGS. 15A-D.

Methodology for mixing independent components to prepare a mixture or administration-ready agent utilizing the assembly illustrated in FIGS. 16A-B can comprise providing a first component in an independent vial 500 and providing a second component to be combined and mixed with the first component within syringe 100. Syringe 100 and vial 500 are then each attached to adapter 700. Attachment and puncturing of vial 500 can be performed as described above with respect to earlier embodiments having puncture device 400. The order of attachment of vial 500 and syringe 100 is not limited to a particular sequence. Preferably, valve 800 is in a closed position during attachments of the vial and the syringe.

Upon assembly, valve 800 can be rotated or otherwise repositioned into an open position to establish fluid communication between first pathway segment 702 and second pathway segment 707 allowing fluid passage through the adaptor. Accordingly, fluid communication is established between vial 500 and syringe 100.

Combining of the first and second components can comprise drawing first component from vial 500 into the syringe (typically with the vial in an inverted position), or can comprise expelling the second component from the syringe into vial 500. Mixture of the components can comprise a pumping action as described above with earlier embodiments independently or in combination with shaking or otherwise agitating the combined components. The resulting mixture can be drawn internally within syringe housing 102e typically while the vial is inverted, and valve 800 can be closed. Where the mixture is to be subsequently transferred or administered to an individual, adaptor 700 can be removed from attachment to Luer-lok fitting 108e and a transfer device such as a needle, cannula, transfer tube or other transfer structure can be attached to Luer-lok device 108e. Transfer or administration of the mixture can then be achieved by expelling the mixture from the internal chamber within syringe housing 102e.

Figure 17:
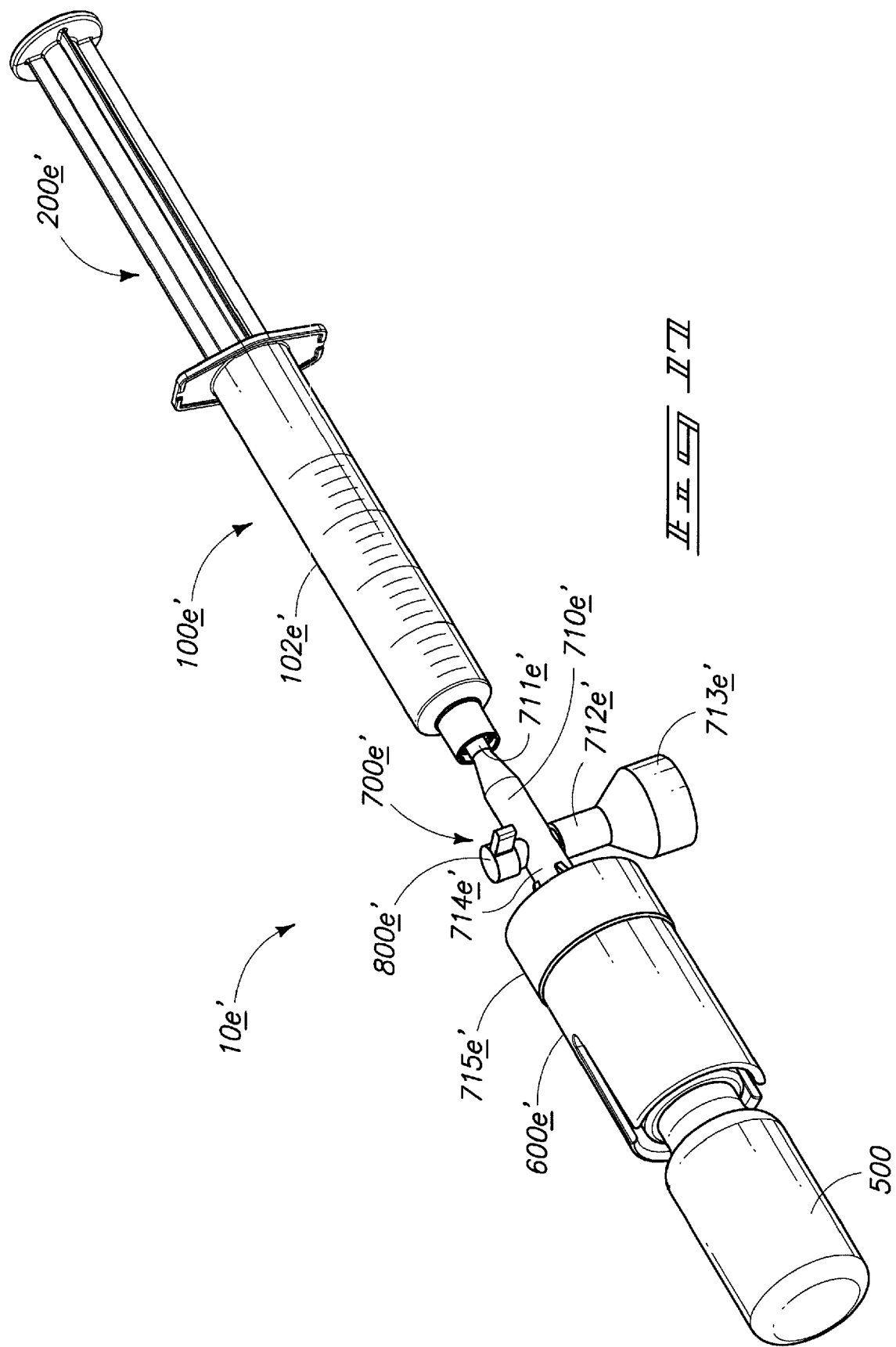
FIG. 17 is a perspective view of an alternate mixing assembly in accordance with one aspect of the invention.

An alternative configuration of an adaptor comprised by an assembly is illustrated in FIG. 17. Assembly 10e' comprises an alternative adaptor configuration 700e' relative to that depicted in FIGS. 16A and 16B. The illustrated adaptor is a "three-way" adaptor having a first segment 710e' which extends from a three-way valve 800e' to a first port 711e' having a fitting (for example a Luer-lok type fitting) for connection with syringe 100e'. Adaptor 700e' additionally includes a second segment 712e' which extends from the position of valve 800e' to a second port 713e'. The adaptor additionally has a third segment 714e' extending from position of valve 800e' to a third port 715e' which can comprise a fitting configured for insertion or other association with housing extension 600e' as illustrated. Port 715e' can additionally be configured to include a piercing structure (not shown) such as the various piercing devices described above. Extension portion 600e' can have any of the configurations described above for receiving, stabilizing and/or retaining vial 500 which is shown in a partially inserted position within extension 600e'. Syringe 100e' can be a standard conventional syringe with an associated standard type piston 200e' as illustrated, or can be an alternative syringe configuration, including but not limited to, those described above.

The triple-port adaptor configuration illustrated in FIG. 17 can advantageously allow introduction and/or removal of material to or from the system without dissociation of the syringe and/or vial 500. For example, after mixing or preparing a medicant utilizing methodology analogous to that described above, the prepared medicant can be transferred or otherwise removed from assembly device 10e' through port 713e'. Such transfer or removal can be accomplished by, for example, attaching an appropriate vial, transfer tubing or other transfer apparatus to port 713e'. As illustrated, port 713e' has a general type fitting. However, a Luer-lok or other alternative fitting can be utilized as appropriate for attachment to a desired container or transfer apparatus.

Transfer of material from the assembly via port 713e' can be useful for applications such as IV administration. Alternative administration such as intramuscular injection, can utilize syringe 100e' independently after removal from the assembly. In either instance, piston depression during injection can be performed manually or utilizing a syringe pump.

Where a material such as a liquid material for example, is to be introduced into assembly 10e' such introduction can be accomplished by passage through port 713e' and adaptor segment 712e'. The fluid introduced can be directed into vial 500 or into syringe 100e' as appropriate, by manipulation and positioning of valve 800e'. Introduction of a fluid into the assembly may be appropriate for example where each of first and second components (within the vial and syringe respectively) is provided in a dry or concentrated form.

The configuration of adaptor 700e' illustrated in FIG. 17 can allow linear alignment of syringe housing 102e' and vial 500. It is to be understood that the invention additionally contemplates configurations having the positions of segments 714e' and 712e' exchanged such that vial 500 and syringe body 102e' are positioned in an orthogonal arrangement. Further, adaptor 700e' can be alternatively configured to provide segments 710e', 712e' and 714e' at alternative angles relative to one another as compared to the orthogonal arrangement shown. Adaptor 700e' can optionally have additional segments and ports and can comprise a higher-order valve relative to the three-way valve depicted.

An additional alternative device configuration in accordance with the invention is described with reference to FIGS. 18A-18C. Referring to FIG. 18A, assembly 10f includes a piston 200f having a rotational type valve portion disposed at second end 204f. Valve portion 226f is functionally and structurally analogous to valve portion 226 as shown in FIG. 15B and as described above. However, rather than being disposed at a junction between two portions of a piston stem as illustrated in FIG. 15B, valve portion 226f is disposed at the end of the piston and is insertable within an opening 557 of a vial cap 550 in accordance with the invention. Vial cap 550 can be configured for utilization in conjunction with a vial such as the exemplary vial 500f depicted in FIG. 18A. Vial 500f can be, for example, a standard medicant vial or alternative container. Vial cap 550 can comprise a base portion 552 and a raised cylindrical or alternatively shaped portion 554 having an opening 557 configured for receiving valve portion 226f of the piston structure.

Upon insertion of valve portion 226f of the piston into receiving opening 557 of cap 550, the lid/piston combination can function as a rotational valve as described above with respect to the rotational valve depicted in FIG. 15.

Referring next to FIG. 18B, grooves 559 provided within interior sidewalls of opening 557 can be aligned with fluid passageways 228f of valve portion 226f. Alignment can provide fluid passageway between passageway 206f through piston 200f and a corresponding fluid passage 560 which passes from opening 557 through base portion 552 of cap 550, thereby allowing fluid passage between a syringe barrel associated with piston 200f and a vial or container associated with cap 552. Fluid alignment and the resulting contiguous passageway is depicted in FIG. 18C. Selective fluid communication can be discontinued by opposing-rotation of piston 200f relative to vial cap 550. In the configuration depicted in FIG. 18A-C, fluid access is provided directly between piston 200f and a vial such that cap 550 can be utilized in an absence of any piercing structure such as the exemplary piercing structure described above.

The invention also contemplates utilization of features of the device shown in FIG. 18 in combination with one or more features described in alternate embodiments above. In particular applications it can be preferable to provide multiple fluid barriers between a syringe barrel and a vial. Accordingly, the rotational valve configuration depicted in FIG. 18 can be utilized in combination with a second rotational valve such as depicted in FIG. 15 or an alternative valve such as described above with reference to earlier figures. Such multiple valve configurations can advantageously provide an additional safeguard against inadvertent contact or mixing of separate components housed within a syringe barrel and the medicant vial. Filters, such as those described above, can additionally be utilized with the device of FIG. 18 and variants thereof.

Methodology for utilization of the assembly configuration depicted in FIGS. 18A-C is analogous to the methodology described above (in an absence of performing steps for piercing a vial cap). Where multiple valves are provided, fluid communication can be established between the syringe barrel and the medicant vial by placing each of the valves in the open position. Mixing can be achieved by, for example, agitation and/or utilization of a piston pumping action. One or both valves can be utilized to discontinue fluid passage, allowing transfer and/or administration of the prepared medicant.

Although various devices of the invention are described as utilizing a single vial 500, it is to be understood that the invention encompasses aspects where multiple vials are utilized. In such instances, a first vial can be removed from the assembly after withdrawing all or a desired portion of the original vial content, and can be replaced by a second vial comprising additional or differing material. Accordingly, the mixing systems of the invention can be utilized for preparing medicants which are made up of three or more components. Mixing of the additional component can be achieved in a manner analogous to the mixing methodology discussed above for a corresponding assembly configuration.

Mixing/administration assemblies in accordance with the invention can be shipped as a singular unit including a linear arrangement of the syringe device and vial. Where an assembly utilizes an independent vial the vial can be provided in or out of alignment with respect to the mixing/administration device. Alternatively, where a vial is independent, such can be packaged separately from the mixing device. Exemplary packaging in accordance with the invention which can be utilized for a linearly aligned vial and mixing device combination is described with reference to FIGS. 19 and 20.

Figure 19:
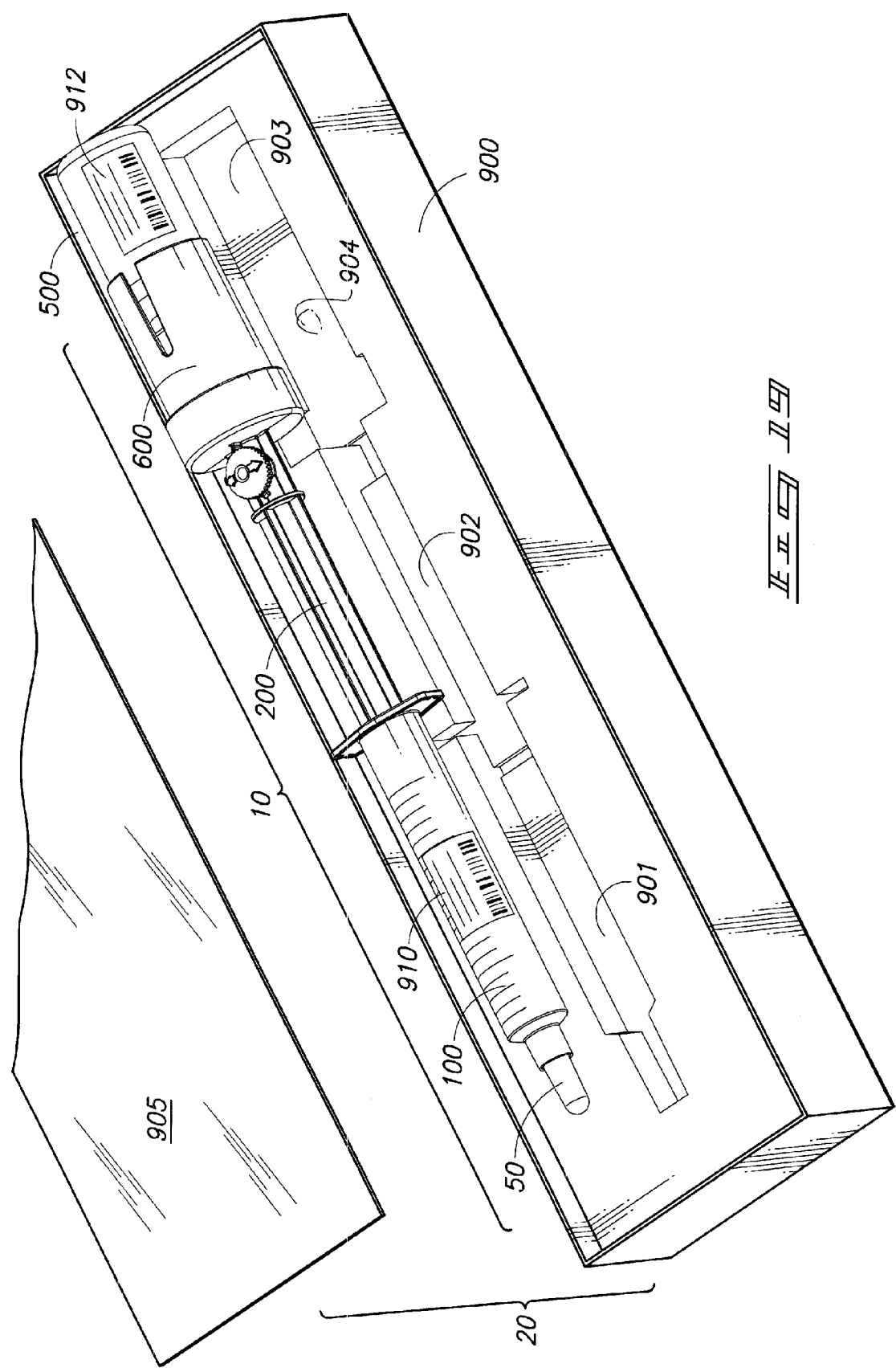
FIG. 19 is a perspective view of a mixing assembly and exemplary packaging in accordance with one aspect of the invention.

As illustrated in FIG. 19 a medicant preparation system 20 in accordance with the invention can comprise a packaging component 900 configured to receive assembly 10 in linear alignment with a vial 500. Packaging component 900 can be a tray type component as illustrated having a multipart cavity 901, 902, 903. Cavity portion 901 can be configured to approximate the shape of syringe 100 and associated cap 50. Cavity portion 902 can be shaped to approximate the shape of piston portion 200. Cavity portion 903 can be shaped to correspond to the shape of the combined extension portion (including the fitting to piston 200 in the illustrated embodiment) and an associated vial 500 which can be partially inserted within housing 600.

In most circumstances it can be preferable that vial 500 be only partially inserted with housing 600. In particular instances it can be highly preferred to avoid contact between the piercing structure comprised by the assembly and the cap or septum comprised by vial 500. Accordingly, a projection 904 can be provided within cavity portion 903 which can be insertable within groove 602 of extension housing 600. Projection 904 can be positioned within the groove to stabilize a spaced relationship between vial 500 and the puncturing device to avoid contact with the piercing structure prior to removal of the assembly from the packaging cavity.

Cavity 901, 902, 903 can be configured to be shaped closely to the shape of the assembly to provide stability to the assembly, preferably stabilizing the position of the piston relative to the syringe barrel. Although the cavities depicted in FIG. 19 mirror the overall shape of the assembly, it is to be understood that the cavity can be alternatively shaped for providing position placement and stability.

Packaging component 900 can be formed by, for example, molding. Appropriate materials for packaging component 900 include plastic materials, preferably plastics which have suitable strength for providing positioning and stability of the packaged assembly.

A cover 905 can optionally be provided which can be associated with packaging component 900. Cover 905 can be provided to cover at least the upper portion/opening of the tray to protect the assembly within the packaging. In particular instances, cover 900 can be utilized to seal the packaging and can allow a sterile environment to be created and maintained within the packaging. The cover can comprise a translucent or opaque material. It can be preferable that at least a portion of the cover be transparent to allow visual inspection of the contents (device and/or labels).

As depicted, cover 905 is a sheet of material which may be affixed to component 900. Alternatively, the cover can be a lid type cover which can be configured either to fit insertably within the tray opening or to have at least an upper portion of the tray fit insertably into a lid cavity (not shown).

As illustrated in FIG. 19, one or more labels 910, 912 can be provided in association with assembly 10. A first label 910 can be utilized in association with the syringe portion of the device and can provide information regarding the contents of the syringe. A second label 912 can be provided associated with vial 500 and can be utilized to identify or provide information regarding the component within the vial. Where the medicant is being provided to a particular individual, one or more of the labels 910 and 912 can contain indicia of the patient. Although FIG. 19 depicts two labels an alternative number of labels can be provided. The content of the information provided in the label is also not limited to any particular content and can provide additional information such as, for example, instructions, warnings, etc. Additionally or alternatively, labeling may be provided in association with packaging component 900 and/or 905 (not shown).

The type of label(s) utilized in association with mixing device 10 and/or associated via 500 is not limited to a particular label type. Exemplary labels can include bar codes as illustrated. Alternatively or additionally, one or both of labels 910 and 912 can be a radio frequency identification (RFID) label (not shown). Appropriate bar code and/or RFID labeling can be particularly useful for identifying and tracking lots, for record keeping purposes regarding the medicants and/or patient specific information. Such labeling can provide an additional safety measure. For example, in the event of an adverse reaction upon administering the prepared medicant, information provided on the label can be utilized to identify source, lot number, etc., which can in turn be utilized to track other assembly devices or device component containing material from the identified lot. Such labeling can additionally be utilized to identify others who may be at risk and/or provide information regarding the particular reaction, etc.

In the event of adverse reaction or identification of defect, analysis of any material retained within the device after administration can be analyzed by, for example, analysis techniques including but not limited to mass spectrometry and/or gas-liquid chromatography. Appropriate reporting to the FDA can then be performed.

Figure 20:
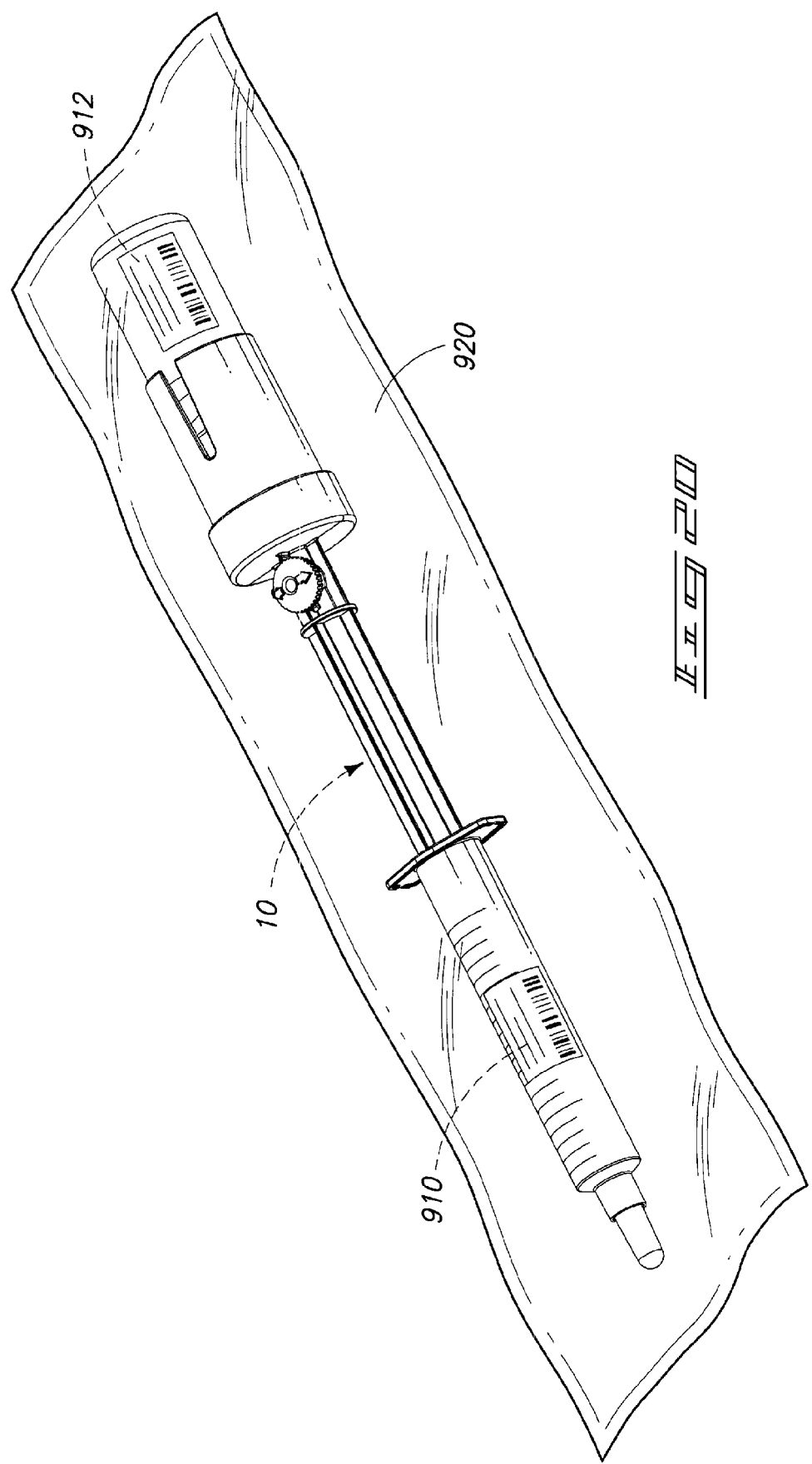
FIG. 20 shows an additional packaging and labeling aspects in accordance with the invention.

Referring to FIG. 20 such shows an additional packaging aspect of the invention. Assembly device 10 can be provided within a second packaging component 920 which can be a sealed pouch type component as illustrated. Packaging component 920 can preferably provide an enclosed environment around device 10 which protects the device and components from exposure to an environment external to packaging component 920. In particular instances, it can be preferable that the internal environment be sterile, especially where medicant components and/or components of system 10 are sterile and are to be maintained in sterile condition prior to administration.

Packaging component 920 can preferably be translucent and can be formed from an appropriate translucent plastic material. The particular material utilized can preferably be selected to provide flexibility to allow manipulation of assembly 10 without opening of packaging component 920. In particular, it can be preferable that component 920 be provided to have sufficient internal volume and material flexibility to allow the vial to be manipulated for engagement and puncturing of the cap/septum. Component 920 can preferably also be retained in the sealed condition while manipulating the valve and piston during combining and mixing of the medicant components (described above). The ability to prepare the medicant for administration without opening of packaging component 920 can minimize or prevent contamination by avoiding exposure to an environment external to the packaging component. Upon preparation of an administration ready medicant, package component 920 can be opened, the protective cap over the forward end of the syringe can be removed, and transfer and/or administration can be performed utilizing methods described above.

Although each can be utilized independently, packaging components 920 and 900 depicted in FIGS. 20 and 19 respectively, are configured to allow utilization of both components for a given device. For example, a mixing device can be enclosed within packaging component 920 and component 920 and its enclosed device can be inserted into the cavity of component 900. Accordingly, component 900 can be utilized to provide positioning and stabilization during shipping and storing. The mixing system can be removed from packaging component 900 while being retained within component 920. The pouch component 920 can be retained in a sealed condition during combination and mixing of the independent components to prepare an administration ready medicant. Where each of components 920 and 900 are utilized, cover 905 can optionally be provided.

Although FIGS. 19 and 20 depict a particular mixing system configuration, it is to be understood that similar packaging concepts can be utilized and adapted for any of the alternative mixing systems described herein.

Each of FIGS. 19 and 20 depict labels associated only to device components. Additional labels (not shown) may be associated with the packaging either by including within the packaging or by affixing externally to the packaging component(s). The additional labeling can be, for example, any of the label types discussed above or alternative labels known to those skilled in the art.

Figure 21:
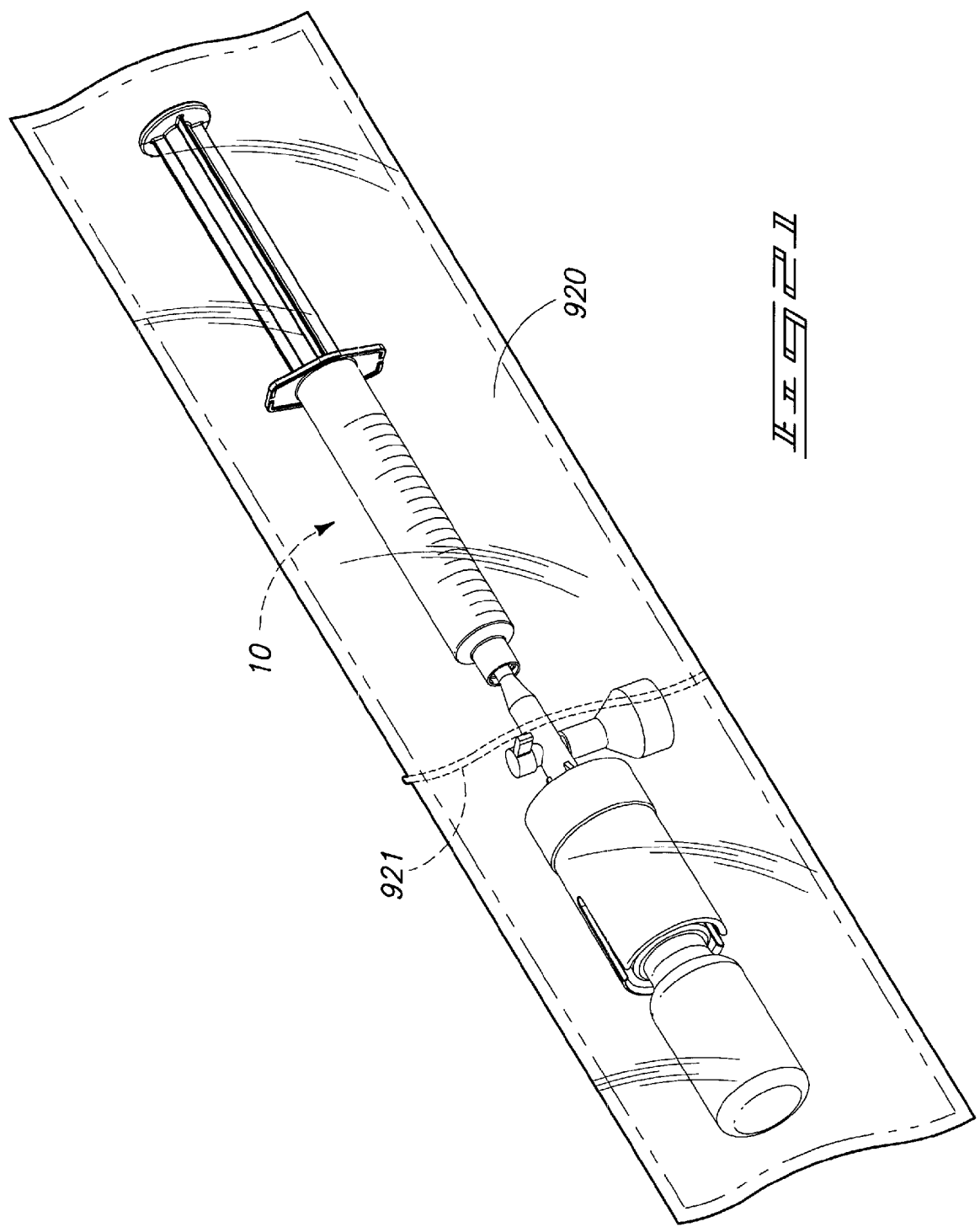
FIG. 21 shows a device and packaging in accordance with an alternate aspect of the invention.

An additional packaging aspect in accordance with the invention is illustrated in FIG. 21. Assembly 10 as illustrated corresponds to the configuration illustrated in FIG. 17 and described with reference thereto. Packaging component 920 corresponds to packaging component 920 discussed above with reference to FIG. 20. As FIG. 21 illustrates, component 920 can be configured to provide access to assembly 10 by a tear strip 921 or alternatively sealed opening. The illustrated packaging configuration can allow mixing and preparation of a medicant in a sealed environment followed by opening of the package along tear strip 921. Where appropriate, the prepared medicant can be transferred from assembly 10 by, for example, attaching an appropriate transfer apparatus to the available port (port 713 as described and illustrated in FIG. 17). Such attachment and transfer can be conducted while all or a portion of assembly 10 remains within the package enclosure.

Where preparation of a medicant involves addition of material into assembly 10 (described above), such material can be added by, for example, opening of tear strip 921 and connection of an appropriate transfer device to the available (non-occupied) port and positioning of the valve to allow introduction of the material into the syringe or vial as appropriate. Additional mixing and preparation steps can be performed as described above with or without removal of assembly 10 from packaging 920. Transfer or administration of a prepared medicant from the assembly can comprise placement of the entire assembly into a syringe pump, can comprise removal of the vial and/or the adaptor from the assembly prior to placement of the syringe into a syringe pump, or can comprise manual manipulation of the syringe piston.

Figure 22:
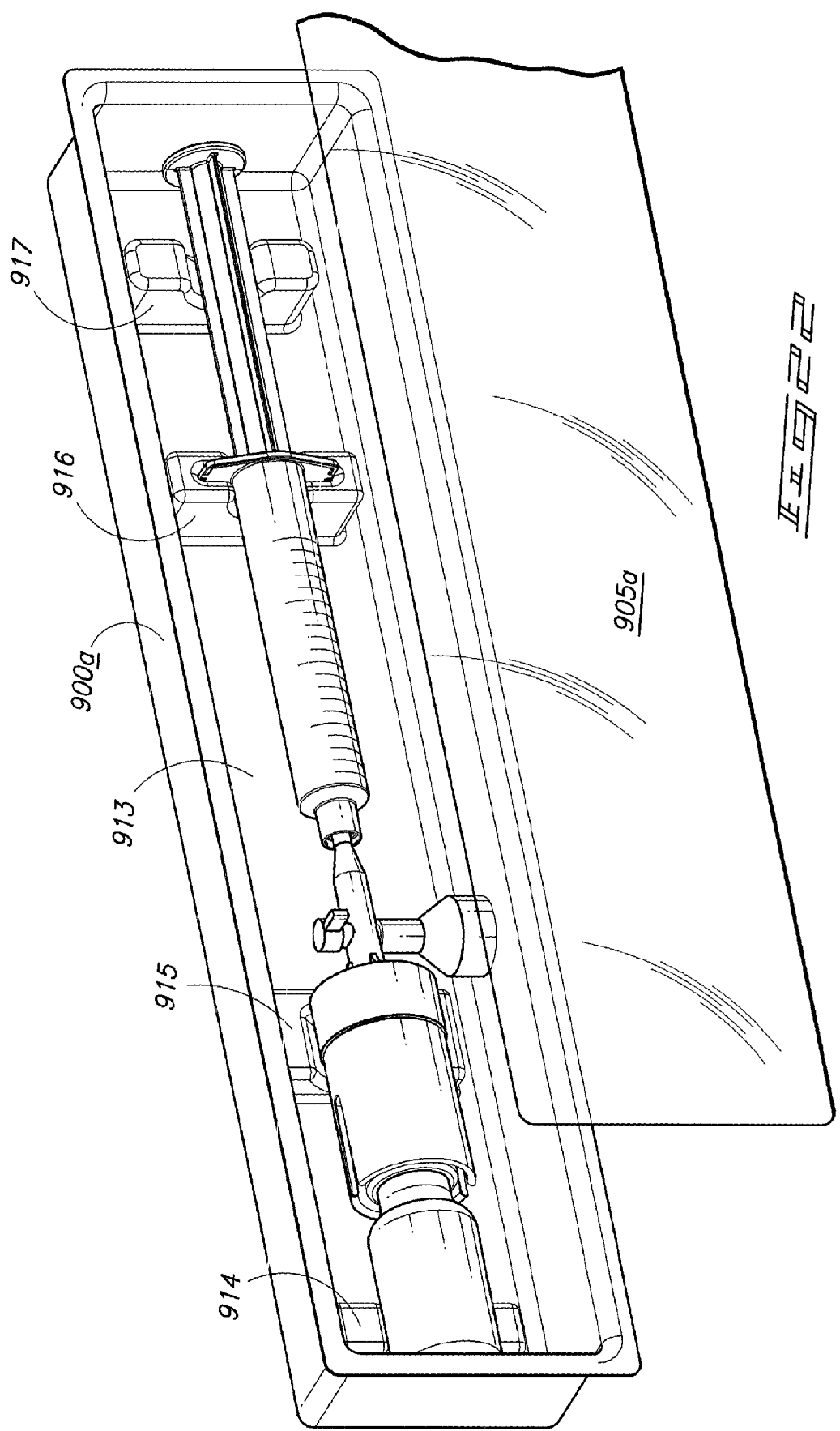
FIG. 22 shows a packaging configuration for a particular aspect of the invention.

An alternative tray-type packaging component 900a is illustrated in FIG. 22. As illustrated, a single cavity 913 can be provided having raised portions 914, 915, 916 and 917. Raised portions 914-917 can be platform-type structures having appropriate shape and positioning to stabilize an inserted mixing assembly. Alternative numbers and positioning of raised portions is contemplated relative to the particular configuration shown in FIG. 22. Packaging 900a can additionally include a raised protrusion (not shown) similar in form and function to protrusion 904 depicted in FIG. 19 and described above. Such protrusion can be configured to insert into a slot present in the extension housing as described above to retain vial 500 in a non-engaged position relative to the piercing structure. Although packaging component 900a is depicted as being configured for the device illustrated in FIG. 17, such can be adapted for any of the alternative embodiments described above. Additionally, packaging component 920 such as illustrated in FIG. 21 can be utilized simultaneously with component 900a by, for example, providing an assembly within packaging component 920 prior to insertion of the assembly into the tray-type component of the packaging.

Packaging component 900a can comprise a lid portion 905a analogous to that shown and described with reference to FIG. 19. Appropriate labeling of assembly components (i.e. vial and/or syringe) can be utilized independently or in addition to labeling of one or more of the packaging components as described previously.

Where an additional material is to be added into the exemplary assembly depicted in FIG. 22, lid 905a, or a portion thereof, can be removed from packaging component 900a followed by opening of a tear strip 921 such as that depicted in FIG. 21. An appropriate transfer device can be connected to the non-occupied port prior to extracting the assembly from the package tray. The introduction of material can be achieved by manipulation of the valve and piston without further removal of the assembly from packaging component 920. Such accessibility to the valve and port can allow introduction of additional materials into the assembly while limiting exposure of the assembly and components therein to an external environment.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A medicant preparation device comprising:
 a syringe barrel having a first end with an extension comprising a male fitting, a second end, and a longitudinal axis therebetween;
 a piston insertable within the syringe barrel through the second end, the piston being slideable within the barrel;
 a vial containing a first component of a medicant material;
 an adapter component comprising:
  a vial housing portion configured to reversibly receive the vial;
  a piercing structure associated with the vial housing, the piercing structure having a head segment comprising a widest portion, a base portion having a first diameter, and a tube segment extending between the head segment and the base portion, the tube segment having a second diameter that is smaller than the first diameter and shorter than the widest portion of the head segment;

a port consisting of a female fitting configured to attach to the syringe at the male fitting at the first end of the syringe barrel;

a valve;

a first fluid passageway extending through the fitting to the valve; and a second fluid passageway extending from the valve to the vial housing; and flexible packaging configured to allow manipulation of the valve and sliding of the piston without opening of the package.

2. The device of claim 1 wherein the first and second passageways are orthogonal relative to each other.

3. The device of claim 1 wherein the adaptor component further comprises a third fluid passageway which extends from the valve, and wherein the valve is a three way valve.

4. The device of claim 1 wherein at least a portion of the packaging comprises a translucent material.

5. The device of claim 1 wherein the packaging comprises a removable portion, wherein prior to the removal of the removable portion at least one of the piston and valve are resistant to manipulation, and wherein removing the removable portion decreases the resistance to manipulation of at least one of the piston and the valve without exposing the syringe barrel, the piston or the adaptor component to an environment external to the packaging.

6. The device of claim 1 wherein the vial containing a first component of a medication agent is contained within the package.

7. The device of claim 6 wherein a second component of the medicant is provided within the syringe barrel.

8. The device of claim 1 wherein the vial having a septum is contained within the package, wherein the packaging allows manipulation of the vial position relative to the piercing structure, and wherein the piercing structure does not contact the septum prior to manipulation.

* * * * *